(12) United States Patent
Luckemeyer et al.

(10) Patent No.: US 9,925,092 B2
(45) Date of Patent: Mar. 27, 2018

(54) ABSORBENT CONDUIT AND SYSTEM

(71) Applicant: KCI Licensing, Inc., San Antonio, TX (US)

(72) Inventors: James A. Luckemeyer, San Antonio, TX (US); Timothy Mark Robinson, Basingstoke (GB); Christopher Brian Locke, Dorset (GB)

(73) Assignee: KCI Licensing, Inc., San Antonio, TX (US)

( * ) Notice: Subject to any disclaimer, the term of this patent is extended or adjusted under 35 U.S.C. 154(b) by 762 days.

(21) Appl. No.: 14/490,870

(22) Filed: Sep. 19, 2014

(65) Prior Publication Data
US 2015/0119830 A1   Apr. 30, 2015

Related U.S. Application Data

(60) Provisional application No. 61/897,669, filed on Oct. 30, 2013.

(51) Int. Cl.
*A61M 1/00* (2006.01)
*A61M 39/00* (2006.01)
(Continued)

(52) U.S. Cl.
CPC .... *A61F 13/0206* (2013.01); *A61F 13/00042* (2013.01); *A61F 13/00051* (2013.01);
(Continued)

(58) Field of Classification Search
CPC ............... A61M 1/0086; A61M 1/0088; A61F 2013/0028; A61F 13/0206; A61F 13/84; A61F 13/00051; A61F 13/00068; A61F 13/00042; A61F 2013/00246; A61F 2013/8408; A61F 2013/00174
See application file for complete search history.

(56) References Cited

U.S. PATENT DOCUMENTS

| 1,355,846 A | 10/1920 | Rannells |
| 1,944,834 A | 1/1934 | Bennett |

(Continued)

FOREIGN PATENT DOCUMENTS

| AU | 550575 A1 | 3/1986 |
| AU | 550575 B2 | 3/1986 |

(Continued)

OTHER PUBLICATIONS

International Search Report and Written Opinion for PCT/GB2008/003075 dated Mar. 11, 2010.

(Continued)

*Primary Examiner* — Adam Marcetich

(57) ABSTRACT

A conduit for treating a tissue site with reduced pressure may include a primary lumen and at least one secondary lumen. A wall of the conduit may include a first wall material and a second wall material. The first wall material may comprise a substantially non-absorbent material that is vapor impermeable and liquid impermeable. The second wall material may comprise an absorbent material that is vapor permeable and liquid impermeable. The second wall material may be positioned in fluid contact with the at least one secondary lumen. Other systems, apparatus, and methods are disclosed.

23 Claims, 8 Drawing Sheets

(51) Int. Cl.
*A61M 39/10* (2006.01)
*A61F 13/02* (2006.01)
*A61F 13/00* (2006.01)
*A61F 13/84* (2006.01)

(52) U.S. Cl.
CPC ........ *A61F 13/00068* (2013.01); *A61F 13/84* (2013.01); *A61M 1/0088* (2013.01); *A61F 2013/00174* (2013.01); *A61F 2013/00246* (2013.01); *A61F 2013/8408* (2013.01)

(56) References Cited

U.S. PATENT DOCUMENTS

| | | |
|---|---|---|
| 2,547,758 A | 4/1951 | Keeling |
| 2,552,664 A | 5/1951 | Burdine |
| 2,632,443 A | 3/1953 | Lesher |
| 2,682,873 A | 7/1954 | Evans et al. |
| 2,860,081 A | 11/1958 | Eiken |
| 2,910,763 A | 11/1959 | Lauterbach |
| 2,969,057 A | 1/1961 | Simmons |
| 3,066,672 A | 12/1962 | Crosby, Jr. et al. |
| 3,172,808 A | 3/1965 | Baumann et al. |
| 3,367,332 A | 2/1968 | Groves |
| 3,376,868 A | 4/1968 | Mondiadis |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,742,952 A | 7/1973 | Magers et al. |
| 3,774,611 A | 11/1973 | Tussey et al. |
| 3,777,016 A | 12/1973 | Gilbert |
| 3,779,243 A | 12/1973 | Tussey et al. |
| 3,826,254 A | 7/1974 | Mellor |
| 3,852,823 A | 12/1974 | Jones |
| 3,903,882 A | 9/1975 | Augurt |
| 3,967,624 A | 7/1976 | Milnamow |
| 3,983,297 A | 9/1976 | Ono et al. |
| 4,060,081 A | 11/1977 | Yannas et al. |
| 4,080,970 A | 3/1978 | Miller |
| 4,096,853 A | 6/1978 | Weigand |
| 4,139,004 A | 2/1979 | Gonzalez, Jr. |
| 4,141,361 A | 2/1979 | Snyder |
| 4,163,822 A | 8/1979 | Walter |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,360,015 A | 11/1982 | Mayer |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,414,970 A | 11/1983 | Berry |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,529,402 A | 7/1985 | Weilbacher et al. |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,600,146 A * | 7/1986 | Ohno ................ A01N 25/18 138/103 |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,652 A | 5/1987 | Weilbacher |
| 4,664,662 A | 5/1987 | Webster |
| 4,710,165 A | 12/1987 | McNeil et al. |
| 4,715,857 A | 12/1987 | Juhasz et al. |
| 4,733,659 A | 3/1988 | Edenbaum et al. |
| 4,743,232 A | 5/1988 | Kruger |
| 4,753,230 A | 6/1988 | Carus et al. |
| 4,758,220 A | 7/1988 | Sundblom et al. |
| 4,787,888 A | 11/1988 | Fox |
| 4,826,494 A | 5/1989 | Richmond et al. |
| 4,832,008 A | 5/1989 | Gilman |
| 4,838,883 A | 6/1989 | Matsuura |
| 4,840,187 A | 6/1989 | Brazier |
| 4,848,364 A | 7/1989 | Bosman |
| 4,863,449 A | 9/1989 | Therriault et al. |
| 4,871,611 A | 10/1989 | LeBel |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,930,997 A | 6/1990 | Bennett |
| 4,941,882 A | 7/1990 | Ward et al. |
| 4,953,565 A | 9/1990 | Tachibana et al. |
| 4,961,493 A | 10/1990 | Kaihatsu |
| 4,969,880 A | 11/1990 | Zamierowski |
| 4,981,474 A | 1/1991 | Bopp et al. |
| 4,985,019 A | 1/1991 | Michelson |
| 4,995,382 A | 2/1991 | Lang et al. |
| 4,996,128 A | 2/1991 | Aldecoa et al. |
| 5,010,883 A | 4/1991 | Rawlings et al. |
| 5,018,515 A | 5/1991 | Gilman |
| 5,028,597 A | 7/1991 | Kodama et al. |
| 5,037,397 A | 8/1991 | Kalt et al. |
| 5,086,170 A | 2/1992 | Luheshi et al. |
| 5,092,323 A | 3/1992 | Riedel et al. |
| 5,092,858 A | 3/1992 | Benson et al. |
| 5,100,396 A | 3/1992 | Zamierowski |
| 5,112,323 A | 5/1992 | Winkler et al. |
| 5,134,994 A | 8/1992 | Say |
| 5,149,331 A | 9/1992 | Ferdman et al. |
| 5,151,314 A | 9/1992 | Brown |
| 5,152,757 A | 10/1992 | Eriksson |
| 5,167,613 A | 12/1992 | Karami et al. |
| 5,176,663 A | 1/1993 | Svedman et al. |
| 5,180,375 A | 1/1993 | Feibus |
| 5,215,522 A | 6/1993 | Page et al. |
| 5,232,453 A | 8/1993 | Plass et al. |
| 5,261,893 A | 11/1993 | Zamierowski |
| 5,266,372 A | 11/1993 | Arakawa et al. |
| 5,270,358 A | 12/1993 | Asmus |
| 5,278,100 A | 1/1994 | Doan et al. |
| 5,279,550 A | 1/1994 | Habib et al. |
| 5,298,015 A | 3/1994 | Komatsuzaki et al. |
| 5,342,329 A | 8/1994 | Croquevielle |
| 5,342,376 A | 8/1994 | Ruff |
| 5,344,415 A | 9/1994 | DeBusk et al. |
| 5,356,386 A | 10/1994 | Goldberg et al. |
| 5,358,494 A | 10/1994 | Svedman |
| 5,384,174 A | 1/1995 | Ward et al. |
| 5,387,207 A | 2/1995 | Dyer et al. |
| 5,419,769 A | 5/1995 | Devlin et al. |
| 5,423,778 A | 6/1995 | Eriksson et al. |
| 5,429,590 A | 7/1995 | Saito et al. |
| 5,437,622 A | 8/1995 | Carion |
| 5,437,651 A | 8/1995 | Todd et al. |
| 5,445,604 A | 8/1995 | Lang |
| 5,447,492 A | 9/1995 | Cartmell et al. |
| 5,458,938 A | 10/1995 | Nygard et al. |
| 5,501,212 A * | 3/1996 | Psaros ................ A61M 16/009 128/204.16 |
| 5,522,808 A | 6/1996 | Skalla |
| 5,527,293 A | 6/1996 | Zamierowski |
| 5,549,584 A | 8/1996 | Gross |
| 5,549,585 A | 8/1996 | Maher et al. |
| 5,556,375 A | 9/1996 | Ewall |

(56) References Cited

U.S. PATENT DOCUMENTS

| | | |
|---|---|---|
| 5,585,178 A | 12/1996 | Calhoun et al. |
| 5,599,292 A | 2/1997 | Yoon |
| 5,607,388 A | 3/1997 | Ewall |
| 5,611,373 A * | 3/1997 | Ashcraft .................. F16L 9/18 138/113 |
| 5,634,893 A | 6/1997 | Rishton |
| 5,636,643 A | 6/1997 | Argenta et al. |
| 5,641,506 A | 6/1997 | Talke et al. |
| 5,645,081 A | 7/1997 | Argenta et al. |
| 5,653,224 A | 8/1997 | Johnson |
| 5,678,564 A | 10/1997 | Lawrence et al. |
| 5,710,233 A | 1/1998 | Meckel et al. |
| 5,714,225 A | 2/1998 | Hansen et al. |
| 5,736,470 A | 4/1998 | Schneberger et al. |
| 5,776,119 A | 7/1998 | Bilbo et al. |
| 5,807,295 A | 9/1998 | Hutcheon et al. |
| 5,878,971 A | 3/1999 | Minnema |
| 5,919,476 A | 7/1999 | Fischer et al. |
| 5,941,863 A | 8/1999 | Guidotti et al. |
| 5,964,252 A | 10/1999 | Simmons et al. |
| 5,981,822 A | 11/1999 | Addison |
| 5,998,561 A | 12/1999 | Jada |
| 6,071,267 A | 6/2000 | Zamierowski |
| 6,086,995 A | 7/2000 | Smith |
| 6,135,116 A | 10/2000 | Vogel et al. |
| 6,174,306 B1 | 1/2001 | Fleischmann |
| 6,191,335 B1 | 2/2001 | Robinson |
| 6,241,747 B1 | 6/2001 | Ruff |
| 6,262,329 B1 | 7/2001 | Brunsveld et al. |
| 6,287,316 B1 | 9/2001 | Agarwal et al. |
| 6,345,623 B1 | 2/2002 | Heaton et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,495,229 B1 | 12/2002 | Carte et al. |
| 6,503,855 B1 | 1/2003 | Menzies et al. |
| 6,548,727 B1 | 4/2003 | Swenson |
| 6,553,998 B2 | 4/2003 | Heaton et al. |
| 6,566,575 B1 | 5/2003 | Stickels et al. |
| 6,566,577 B1 | 5/2003 | Addison et al. |
| 6,626,891 B2 | 9/2003 | Ohmstede |
| 6,627,215 B1 | 9/2003 | Dale et al. |
| 6,648,862 B2 | 11/2003 | Watson |
| 6,680,113 B1 | 1/2004 | Lucast et al. |
| 6,685,681 B2 | 2/2004 | Lockwood et al. |
| 6,693,180 B2 | 2/2004 | Lee et al. |
| 6,695,823 B1 | 2/2004 | Lina et al. |
| 6,752,794 B2 | 6/2004 | Lockwood et al. |
| 6,787,682 B2 | 9/2004 | Gilman |
| 6,814,079 B2 | 11/2004 | Heaton et al. |
| 6,855,135 B2 | 2/2005 | Lockwood et al. |
| 6,856,821 B2 | 2/2005 | Johnson |
| 6,979,324 B2 | 12/2005 | Bybordi et al. |
| 7,070,584 B2 | 7/2006 | Johnson et al. |
| 7,154,017 B2 | 12/2006 | Sigurjonsson et al. |
| 7,402,721 B2 | 7/2008 | Sigurjonsson et al. |
| 7,569,742 B2 | 8/2009 | Haggstrom et al. |
| 7,645,269 B2 | 1/2010 | Zamierowski |
| 8,298,197 B2 | 10/2012 | Eriksson et al. |
| 8,529,532 B2 | 9/2013 | Pinto et al. |
| 8,632,523 B2 | 1/2014 | Eriksson et al. |
| 8,764,732 B2 | 7/2014 | Hertwell |
| 9,192,444 B2 | 11/2015 | Locke et al. |
| 2001/0030304 A1 | 10/2001 | Kohda et al. |
| 2001/0051178 A1 | 12/2001 | Blatchford et al. |
| 2002/0009568 A1 | 1/2002 | Bries et al. |
| 2002/0016346 A1 | 2/2002 | Brandt et al. |
| 2002/0065494 A1 | 5/2002 | Lockwood et al. |
| 2002/0077661 A1 | 6/2002 | Saadat |
| 2002/0115951 A1 | 8/2002 | Norstrem et al. |
| 2002/0119292 A1 | 8/2002 | Venkatasanthanam et al. |
| 2002/0120185 A1 | 8/2002 | Johnson |
| 2002/0130064 A1 | 9/2002 | Adams et al. |
| 2002/0143286 A1 | 10/2002 | Tumey |
| 2002/0150270 A1 | 10/2002 | Werner |
| 2002/0150720 A1 | 10/2002 | Howard et al. |
| 2002/0161346 A1 | 10/2002 | Lockwood et al. |
| 2002/0164346 A1 | 11/2002 | Nicolette |
| 2002/0183702 A1 | 12/2002 | Henley et al. |
| 2002/0198504 A1 | 12/2002 | Risk et al. |
| 2003/0014022 A1 | 1/2003 | Lockwood et al. |
| 2003/0109855 A1 | 6/2003 | Solem et al. |
| 2003/0158577 A1 | 8/2003 | Ginn et al. |
| 2003/0212357 A1 | 11/2003 | Pace |
| 2003/0225347 A1 | 12/2003 | Argenta et al. |
| 2003/0225355 A1 | 12/2003 | Butler |
| 2004/0002676 A1 | 1/2004 | Siegwart et al. |
| 2004/0030304 A1 | 2/2004 | Hunt et al. |
| 2004/0064132 A1 | 4/2004 | Boehringer et al. |
| 2004/0077984 A1 | 4/2004 | Worthley |
| 2004/0099268 A1 * | 5/2004 | Smith .................. A61M 16/08 128/203.16 |
| 2004/0118401 A1 * | 6/2004 | Smith .................. A61M 16/08 128/204.17 |
| 2004/0127836 A1 | 7/2004 | Sigurjonsson et al. |
| 2004/0127862 A1 | 7/2004 | Bubb et al. |
| 2004/0133143 A1 | 7/2004 | Burton et al. |
| 2004/0186239 A1 | 9/2004 | Qin et al. |
| 2004/0219337 A1 | 11/2004 | Langley et al. |
| 2004/0230179 A1 | 11/2004 | Shehada |
| 2005/0034731 A1 | 2/2005 | Rousseau et al. |
| 2005/0054998 A1 | 3/2005 | Poccia et al. |
| 2005/0059918 A1 | 3/2005 | Sigurjonsson et al. |
| 2005/0065484 A1 | 3/2005 | Watson |
| 2005/0070858 A1 | 3/2005 | Lockwood et al. |
| 2005/0101940 A1 | 5/2005 | Radl et al. |
| 2005/0113732 A1 | 5/2005 | Lawry |
| 2005/0124925 A1 | 6/2005 | Scherpenborg |
| 2005/0131327 A1 | 6/2005 | Lockwood et al. |
| 2005/0137539 A1 | 6/2005 | Biggie et al. |
| 2005/0143694 A1 | 6/2005 | Schmidt et al. |
| 2005/0159695 A1 | 7/2005 | Cullen et al. |
| 2005/0161042 A1 * | 7/2005 | Fudge .................. A61B 5/097 128/205.12 |
| 2005/0163978 A1 | 7/2005 | Strobech et al. |
| 2005/0214376 A1 * | 9/2005 | Faure .................. A61K 9/0014 424/486 |
| 2005/0233072 A1 | 10/2005 | Stephan et al. |
| 2005/0256437 A1 | 11/2005 | Silcock et al. |
| 2005/0261642 A1 | 11/2005 | Weston |
| 2005/0261643 A1 | 11/2005 | Bybordi et al. |
| 2005/0277860 A1 | 12/2005 | Jensen |
| 2006/0079852 A1 | 4/2006 | Bubb et al. |
| 2006/0083776 A1 | 4/2006 | Bott et al. |
| 2006/0154546 A1 | 7/2006 | Murphy et al. |
| 2006/0236979 A1 * | 10/2006 | Stolarz .................. B60K 15/01 123/468 |
| 2006/0241542 A1 | 10/2006 | Gudnason et al. |
| 2006/0271020 A1 | 11/2006 | Huang et al. |
| 2007/0027414 A1 | 2/2007 | Hoffman et al. |
| 2007/0078366 A1 | 4/2007 | Haggstrom et al. |
| 2007/0185426 A1 | 8/2007 | Ambrosio et al. |
| 2007/0225663 A1 | 9/2007 | Watt et al. |
| 2007/0265585 A1 | 11/2007 | Joshi et al. |
| 2007/0265586 A1 | 11/2007 | Joshi et al. |
| 2008/0027366 A1 | 1/2008 | Da Silva Macedo |
| 2008/0090085 A1 | 4/2008 | Kawate et al. |
| 2008/0119802 A1 | 5/2008 | Riesinger |
| 2008/0138591 A1 | 6/2008 | Graham et al. |
| 2008/0149104 A1 | 6/2008 | Eifler |
| 2008/0195017 A1 | 8/2008 | Robinson et al. |
| 2008/0225663 A1 | 9/2008 | Smith et al. |
| 2008/0243044 A1 | 10/2008 | Hunt et al. |
| 2008/0269657 A1 | 10/2008 | Brenneman et al. |
| 2008/0271804 A1 | 11/2008 | Biggie et al. |
| 2009/0025724 A1 * | 1/2009 | Herron, Jr. ........ A61M 16/0808 128/204.18 |
| 2009/0088719 A1 | 4/2009 | Driskell |
| 2009/0093779 A1 | 4/2009 | Riesinger |
| 2009/0124988 A1 | 5/2009 | Coulthard |
| 2009/0177172 A1 | 7/2009 | Wilkes |
| 2009/0216204 A1 | 8/2009 | Bhavaraju et al. |
| 2009/0227969 A1 | 9/2009 | Jaeb et al. |
| 2009/0264807 A1 | 10/2009 | Haggstrom et al. |

(56) References Cited

U.S. PATENT DOCUMENTS

| | | | |
|---|---|---|---|
| 2009/0292264 A1* | 11/2009 | Hudspeth | A61M 1/0088 604/313 |
| 2009/0312662 A1* | 12/2009 | Colman | A61B 5/097 600/543 |
| 2009/0326488 A1 | 12/2009 | Budig et al. | |
| 2010/0063467 A1 | 3/2010 | Addison et al. | |
| 2010/0106106 A1 | 4/2010 | Heaton et al. | |
| 2010/0106118 A1* | 4/2010 | Heaton | A61M 1/0088 604/319 |
| 2010/0125259 A1 | 5/2010 | Olson | |
| 2010/0159192 A1 | 6/2010 | Cotton | |
| 2010/0185163 A1 | 7/2010 | Heagle | |
| 2010/0226824 A1* | 9/2010 | Ophir | A61M 16/0875 422/84 |
| 2010/0262090 A1 | 10/2010 | Riesinger | |
| 2010/0267302 A1 | 10/2010 | Kantner et al. | |
| 2010/0305490 A1 | 12/2010 | Coulthard et al. | |
| 2010/0305524 A1 | 12/2010 | Vess et al. | |
| 2010/0324516 A1 | 12/2010 | Braga et al. | |
| 2011/0046585 A1 | 2/2011 | Weston | |
| 2011/0137271 A1 | 6/2011 | Andresen et al. | |
| 2011/0160686 A1 | 6/2011 | Ueda et al. | |
| 2011/0171480 A1 | 7/2011 | Mori et al. | |
| 2011/0172617 A1 | 7/2011 | Riesinger | |
| 2011/0224631 A1 | 9/2011 | Simmons et al. | |
| 2011/0229688 A1 | 9/2011 | Cotton | |
| 2011/0244010 A1 | 10/2011 | Doshi | |
| 2011/0257617 A1 | 10/2011 | Franklin | |
| 2012/0016322 A1 | 1/2012 | Coulthard et al. | |
| 2012/0123359 A1* | 5/2012 | Reed | A61M 1/008 604/319 |
| 2012/0143157 A1 | 6/2012 | Riesinger | |
| 2012/0258271 A1 | 10/2012 | Maughan | |
| 2013/0030394 A1 | 1/2013 | Locke et al. | |
| 2013/0066285 A1 | 3/2013 | Locke et al. | |
| 2013/0096518 A1 | 4/2013 | Hall et al. | |
| 2013/0152945 A1 | 6/2013 | Locke et al. | |
| 2014/0039423 A1 | 2/2014 | Riesinger | |
| 2014/0039424 A1 | 2/2014 | Locke | |
| 2014/0155849 A1 | 6/2014 | Heaton et al. | |
| 2014/0171851 A1 | 6/2014 | Addison | |
| 2014/0309574 A1 | 10/2014 | Cotton | |
| 2014/0350494 A1 | 11/2014 | Hartwell et al. | |
| 2015/0030848 A1 | 1/2015 | Goubard | |
| 2015/0119830 A1 | 4/2015 | Luckemeyer et al. | |
| 2015/0190286 A1* | 7/2015 | Allen | A61F 13/0206 604/319 |
| 2016/0000610 A1 | 1/2016 | Riesinger | |
| 2016/0067107 A1 | 3/2016 | Cotton | |
| 2016/0144084 A1 | 5/2016 | Collinson et al. | |

FOREIGN PATENT DOCUMENTS

| | | |
|---|---|---|
| AU | 745271 | 4/1999 |
| AU | 755496 | 2/2002 |
| AU | 745271 B2 | 3/2002 |
| AU | 755496 B2 | 12/2002 |
| AU | 2009200608 A1 | 10/2009 |
| CA | 2005436 | 6/1990 |
| CA | 2005436 A1 | 6/1990 |
| CN | 87101823 A | 8/1988 |
| DE | 26 40 413 A1 | 3/1978 |
| DE | 43 06 478 A1 | 9/1994 |
| DE | 29 504 378 U1 | 9/1995 |
| DE | 295 04 378 U1 | 10/1995 |
| DE | 202004018245 U1 | 7/2005 |
| EP | 097517 A1 | 1/1984 |
| EP | 0100148 A1 | 2/1984 |
| EP | 0117632 A2 | 9/1984 |
| EP | 0147119 A2 | 7/1985 |
| EP | 0161865 A2 | 11/1985 |
| EP | 0251810 A2 | 1/1988 |
| EP | 0275353 A2 | 7/1988 |
| EP | 0358302 A2 | 3/1990 |
| EP | 0538917 A1 | 4/1993 |
| EP | 0630629 A1 | 12/1994 |
| EP | 0659390 A2 | 6/1995 |
| EP | 0633758 B1 | 10/1996 |
| EP | 1002846 A1 | 5/2000 |
| EP | 1018967 A1 | 7/2000 |
| EP | 1018967 B1 | 8/2004 |
| EP | 2578193 A1 | 4/2013 |
| GB | 692578 | 6/1953 |
| GB | 692578 A | 6/1953 |
| GB | 1386800 A | 3/1975 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 329 127 B | 3/1999 |
| GB | 2 333 965 A | 8/1999 |
| GB | 2377939 A | 1/2003 |
| GB | 2392836 A | 3/2004 |
| GB | 2393655 A | 4/2004 |
| GB | 2425487 A | 11/2006 |
| GB | 2452720 A | 3/2009 |
| GB | 2496310 A | 5/2013 |
| JP | 1961003393 | 2/1961 |
| JP | S62139523 U | 9/1987 |
| JP | S62-275456 A | 11/1987 |
| JP | 4129536 | 4/1992 |
| JP | 2007254515 A | 10/2007 |
| JP | 2008080137 A | 4/2008 |
| JP | 4129536 B2 | 8/2008 |
| SG | 71559 | 3/1999 |
| SG | 71559 | 4/2002 |
| WO | 80/02182 A1 | 10/1980 |
| WO | 87/04626 A1 | 8/1987 |
| WO | 8707164 A1 | 12/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 9622753 A1 | 8/1996 |
| WO | 97/18007 A1 | 5/1997 |
| WO | 99/13793 A1 | 3/1999 |
| WO | 99/65542 A1 | 12/1999 |
| WO | 01019306 A1 | 3/2001 |
| WO | 01/36188 A1 | 5/2001 |
| WO | 01/60296 A1 | 8/2001 |
| WO | 0168021 A1 | 9/2001 |
| WO | 0185248 | 11/2001 |
| WO | 0185248 A1 | 11/2001 |
| WO | 01085248 A1 | 11/2001 |
| WO | 0243743 A1 | 6/2002 |
| WO | 02062403 A1 | 8/2002 |
| WO | 03-018098 A2 | 3/2003 |
| WO | 03045294 A1 | 6/2003 |
| WO | 03045492 A1 | 6/2003 |
| WO | 03053484 A1 | 7/2003 |
| WO | 2004024197 A1 | 3/2004 |
| WO | 2004037334 A1 | 5/2004 |
| WO | 2004112852 A1 | 12/2004 |
| WO | 2005002483 A2 | 1/2005 |
| WO | 2005062896 A2 | 7/2005 |
| WO | 2005105176 A1 | 11/2005 |
| WO | 2005123170 A1 | 12/2005 |
| WO | 2007022097 A2 | 2/2007 |
| WO | 2007030601 A2 | 3/2007 |
| WO | 2007070269 A1 | 6/2007 |
| WO | 2007085396 A1 | 8/2007 |
| WO | 2007087811 A1 | 8/2007 |
| WO | 2007113597 A2 | 10/2007 |
| WO | 2007133618 A2 | 11/2007 |
| WO | 2008026117 A1 | 3/2008 |
| WO | 2008041926 A1 | 4/2008 |
| WO | 2008054312 A1 | 5/2008 |
| WO | 2008/082444 A2 | 7/2008 |
| WO | 2008100440 A1 | 8/2008 |
| WO | 2008104609 A1 | 9/2008 |
| WO | 2008/131895 A1 | 11/2008 |
| WO | 2009/002260 A1 | 12/2008 |

(56) References Cited

FOREIGN PATENT DOCUMENTS

| WO | 2008149107 A1 | 12/2008 |
|---|---|---|
| WO | 2009066105 A1 | 5/2009 |
| WO | 2009066106 A1 | 5/2009 |
| WO | 2009081134 A1 | 7/2009 |
| WO | 2009089016 A1 | 7/2009 |
| WO | 2009/124100 A1 | 10/2009 |
| WO | 2009126103 A1 | 10/2009 |
| WO | 2010032728 A1 | 3/2010 |
| WO | 2010/056977 A2 | 5/2010 |
| WO | 2010129299 A2 | 11/2010 |
| WO | 2011008497 A2 | 1/2011 |
| WO | 2011/049562 A1 | 4/2011 |
| WO | 2011043786 A1 | 4/2011 |
| WO | 2011115908 A1 | 9/2011 |
| WO | 2011121127 A1 | 10/2011 |
| WO | 2011162862 A1 | 12/2011 |
| WO | 2012/112204 A1 | 8/2012 |
| WO | 2012104584 A1 | 8/2012 |
| WO | 2012140378 A1 | 10/2012 |
| WO | 2012143665 A1 | 10/2012 |
| WO | 2013009239 A1 | 1/2013 |
| WO | 2013090810 A1 | 6/2013 |
| WO | 2014039557 A1 | 3/2014 |
| WO | 2014078518 A1 | 5/2014 |
| WO | 2014/113253 A1 | 7/2014 |
| WO | 2014140608 A1 | 9/2014 |
| WO | 2014143488 A1 | 9/2014 |
| WO | 2015/065615 A1 | 5/2015 |
| WO | 2015130471 A1 | 9/2015 |
| WO | 2017048866 A1 | 3/2017 |

OTHER PUBLICATIONS

International Search Report and Written Opinion for PCT/GB2008/004216 dated Jul. 2, 2009.
International Search Report and Written Opinion for PCT/GB2012/000099 dated May 2, 2012.
EP Examination Report dated May 22, 2014 for EP.
International Search Report and Written Opinion for PCT/US2012/069893 dated Apr. 8, 2013.
International Search Report and Written Opinion for PCT/US2013/070070 dated Jan. 29, 2014.
International Search Report and Written Opinion for PCT/US2014/016320 dated Apr. 15, 2014.
International Search Report and Written Opinion for PCT/US2014/056508 dated Dec. 9, 2014.
International Search Report and Written Opinion for PCT/US2014/056524 dated Dec. 11, 2014.
International Search Report and Written Opinion for PCT/US2014/056594 dated Dec. 2, 2014.
Partial International Search Report dated Jul. 31, 2009; PCT Internationl Application No. PCT/US2009/036222.
International Search Report and Written opinion dated Dec. 15, 2009; PCT Internation Application No. PCT/US2009/036222.
International Search Report and Written Opinion dated Feb. 24, 2010; PCT/US2009/057182.
International Search Report and Written Opinion dated Jan. 5, 2010; PCT International Application No. PCT/US2009/057130.
Response filed Oct. 20, 2011 for U.S. Appl. No. 12/398,904.
Interview Summary dated Oct. 27, 2011 for U.S. Appl. No. 12/398,904.
Non-Final Office Action dated Jul. 20, 2011 for U.S. Appl. No. 12/398,904.
V.A. Solovev et al., Guidelines, The Method of Treatment of Immagure External Fistulas in the Upper Gastrointestinal Tract, editor-in-chief Prov. V.I. Parahonyak (S.M. Kirov Gorky State Medican Institute, Gorky, U.S.S.R. 1987) ("Solovev Guidelines").
V.A. Kuznetsov & N.a. Bagautdinov, "Vacuum and Vacuum-Sorption Treatement of Open Septic Wounds," in All-Union Conference on Wounds and Wound Infections: Presentation Abstracts, edited by B.M. Kostyuchenok et al. (Masco, U.S.S.R. Oct. 28-29, 1986) pp. 91-92 ("Bagautdinov II").

V.A. Solovev, Dissertation Abstract, Treatement and Prevention of Suture Failures after Gastric Resection (S.M. Kirov Gorky State Medical Institute, Gorky, U.S.S.R. 1998 ("Solovev Abstract").
Partial International Search Report dated Jul. 31, 2009 for PCT International Application No. PCT/US2009/036217.
International Search Report and Written Opinion dated May 31, 2010 for PCT Application No. PCT/US2009/064364.
Examination report for AU2009221772 dated Apr. 4, 2013.
Response filed Oct. 21, 2011 for U.S. Appl. No. 12/398,891.
Interview Summary dated Oct. 27, 2011 for U.S. Appl. No. 12/398,891.
Restriction Requirement dated Jun. 13, 2011 for U.S. Appl. No. 12/398,891.
Response filed Jun. 24, 2011 for U.S. Appl. No. 12/398,891.
Non-Final Office Action dated Jul. 21, 2011 for U.S. Appl. No. 12/398,891.
International Search Report and Written Opinion dated Oct. 19, 2010; PCT International Application No. PCT/US2009/036217.
International Search Report and Written Opinion dated Feb. 24, 2010; PCT International Application No. PCT/US2009/057182.
Partial International Search Report dated Jul. 31, 2009; PCT Internationl Application No. PCT/US2009/036222.
Non-Final Rejection for U.S. Appl. No. 12/398,904 dated Mar. 14, 2012.
Response to Non-Final Rejection for U.S. Appl. No. 12/398,904, filed Jun. 4, 2012.
International Search Report and Written Opinion for PCT/US2014/061251 dated May 8, 2015.
International Search Report and Written Opinion for PCT/IB2013/060862 dated Jun. 26, 2014.
International Search Report and Written Opinion for PCT/US2015/015493 dated May 4, 2015.
European Search Report for corresponding Application No. 15194949.2.
European Search Report for corresponding EPSN 15157408.4 published on Sep. 30, 2015.
International Search Report and Written Opinion for PCT/US2015/034289 dated Aug. 21, 2015.
International Search Report and Written Opinion for PCT/US2015/065135 dated Apr. 4, 2016.
International Search Report and Written Opinion for PCT/GB2012/050822 dated Aug. 8, 2012.
International Search Report and Written Opinion for PCT/US2015/029037 dated Sep. 4, 2015.
International Search Report and Written Opinion dated Jun. 1, 2011 for PCT International Application No. PCT/US2011/028344.
European Search Report for EP 11714148.1, dated May 2, 2014.
European Search Report for corresponding Application No. 15192606.0 dated Feb. 24, 2016.
International Search Report and Written Opinion for corresponding PCT/US2014/048081 dated Nov. 14, 2014.
International Search Report and Written Opinion for corresponding PCT/US2014/010704 dated Mar. 25, 2014.
European Examination Report dated Jun. 29, 2016, corresponding to EP Application No. 16173614.5.
International Search Report and Written Opinion for corresponding PCT application PCT/US2016/051768 dated Dec. 15, 2016.
International Search Report and Written Opinion for corresponding PCT/US2014/056566, dated Dec. 5, 2014.
N. A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.

(56) References Cited

OTHER PUBLICATIONS

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovic, V. Đukić, Ž. Maksimović, Đ.. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul. 2007).

European Search Report for corresponding EP Application 171572787 dated Jun. 6, 2017.

International Search Report and Written Opinion for corresponding application PCT/US2016/031397.

European Search Report for corresponding application 17167872.5, dated Aug. 14, 2017.

NPD 1000 Negative Pressure Would Therapy System, Kalypto Medical, pp. 1-4, dated Sep. 2008.

M. Waring et al., "Cell attachment to adhesive dressing: qualitative and quantitative analysis", Wounds, UK, (2008), vol. 4, No. 3, pp. 35-47.

R. White, "Evidence for atraumatic soft silicone wound dressing use". Wound, UK (2005), vol. 3, pp. 104-108, Mepilex Border docs, (2001).

European Search Report for corresponding application 17183683.6, dated Sep. 18, 2017.

European Search Report for corresponding application 17164033.7, dated Oct. 13, 2017.

Extended European Search Report for corresponding application 17191970.7, dated Oct. 26, 2017.

Office Action for related U.S. Appl. No. 13/982,650, dated Dec. 14, 2017.

Australian Office Action for related application 2013344686, dated Nov. 28, 2017.

Office Action for related U.S. Appl. No. 14/517,521, dated Dec. 12, 2017.

Office Action for related U.S. Appl. No. 14/490,898, dated Jan. 4, 2018.

International Search Report and Written Opinion for PCT/US2017/058209, dated Jan. 10, 2018.

Office Action for related U.S. Appl. No. 14/965,675, dated Jan. 31, 2018.

\* cited by examiner

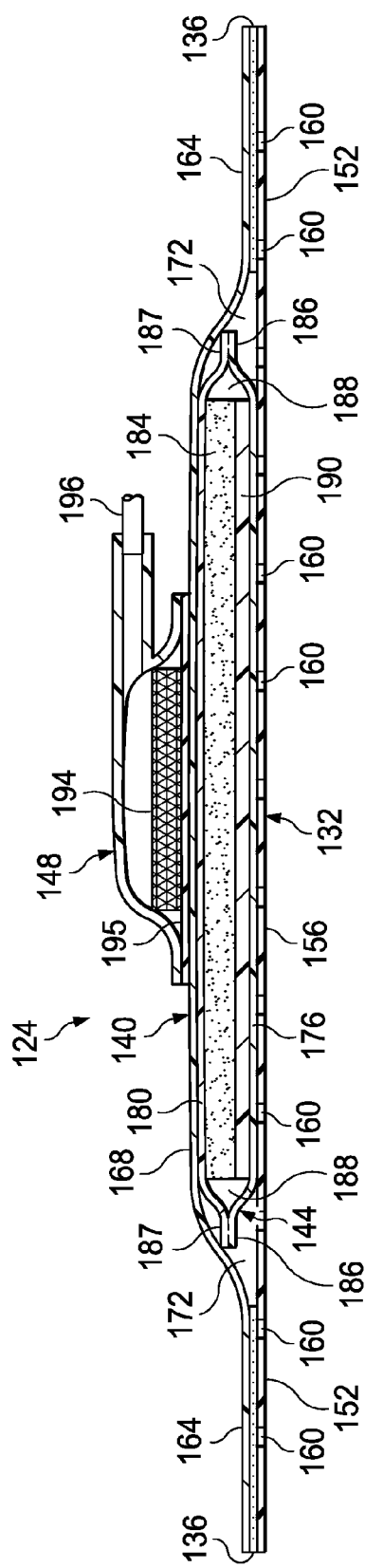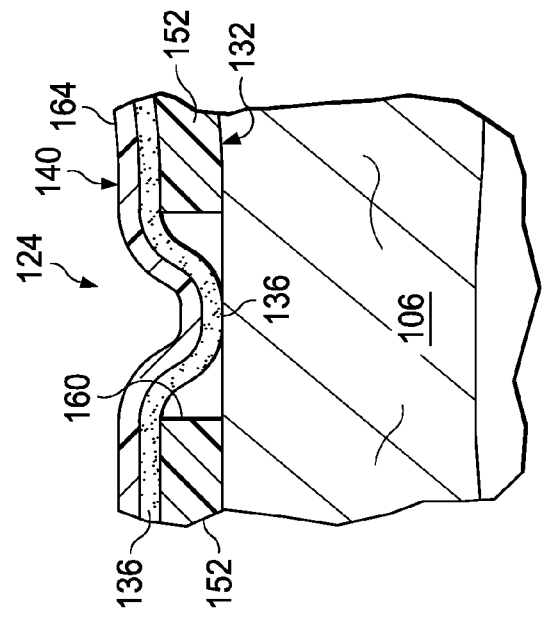

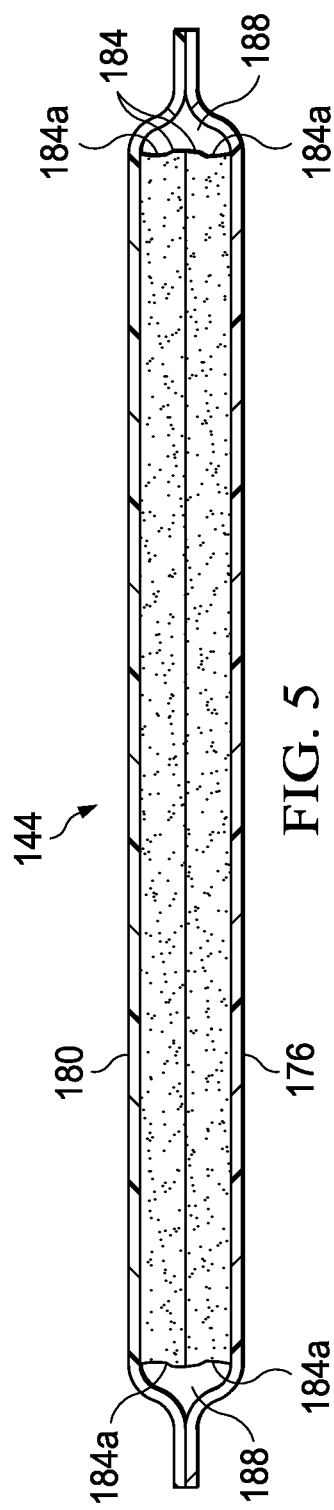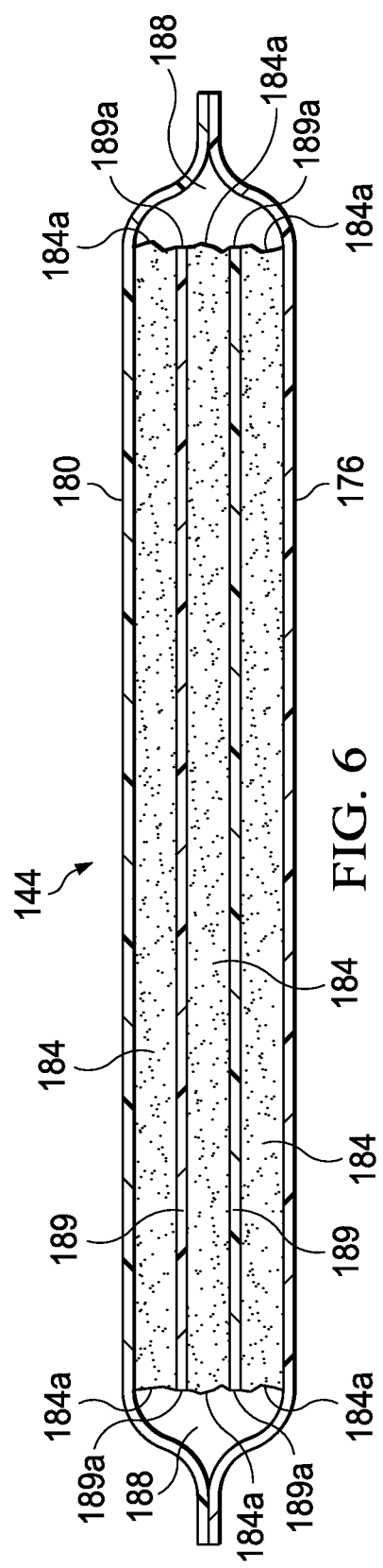

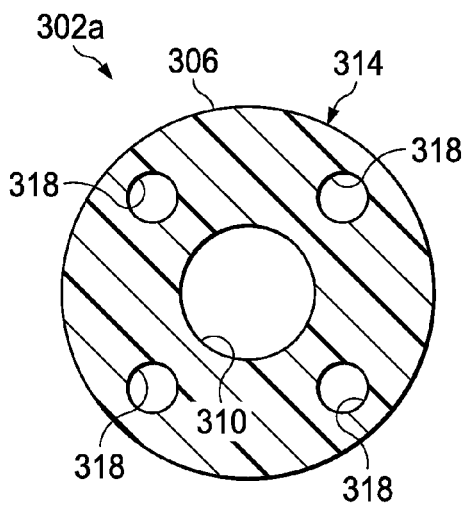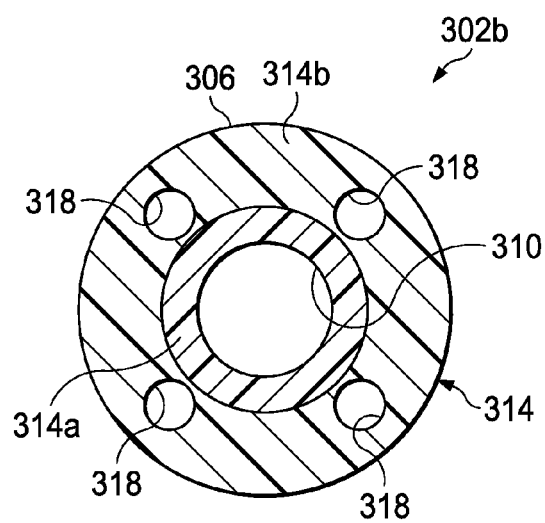
FIG. 9A            FIG. 9B
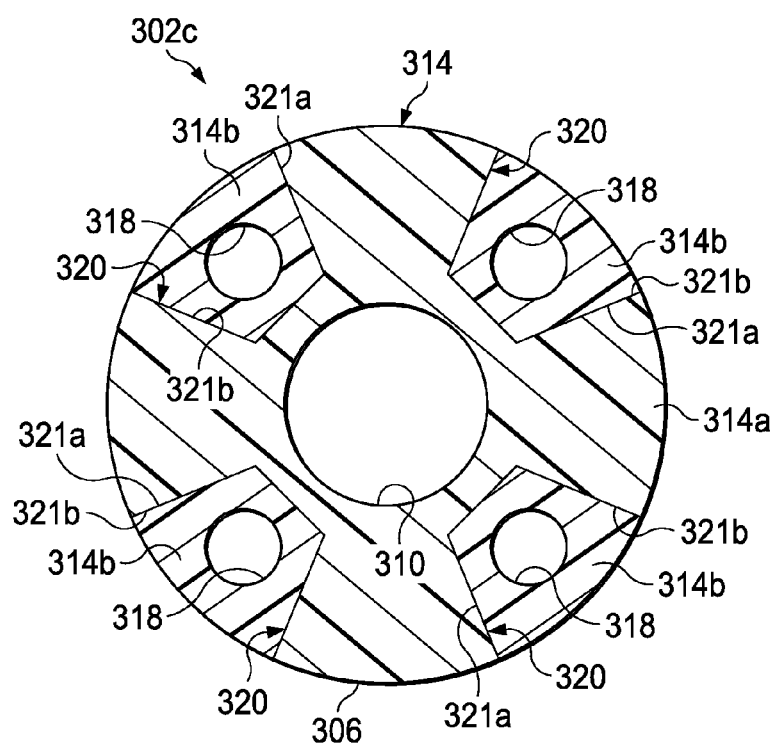
FIG. 9C

ABSORBENT CONDUIT AND SYSTEM

RELATED APPLICATION

This disclosure claims the benefit, under 35 USC § 119(e), of the filing of U.S. Provisional Patent Application Ser. No. 61/897,669, entitled "ABSORBENT CONDUIT AND SYSTEM," filed Oct. 30, 2013, which is incorporated herein by reference for all purposes.

FIELD

This disclosure relates generally to medical treatment systems and, more particularly, but not by way of limitation, to absorbent dressings, systems, and methods for treating a tissue site with reduced pressure.

BACKGROUND

Depending on the medical circumstances, reduced pressure may be used for, among other things, reduced-pressure therapy to encourage granulation at a tissue site, draining fluids at a tissue site, closing a wound, reducing edema, promoting perfusion, and fluid management. Common dressings, systems, and methods may be susceptible to leaks and blockage that can cause a reduction in the efficiency of the therapy or a complete loss of therapy. Such a situation can occur, for example, if the amount of fluid in the dressing or system exceeds the fluid capacity of the dressing or system. Further, the formation of condensate in the dressing or system may create similar concerns. Leaks, blockages, and condensate in the dressing or system may also be perceptible by a user and may lack visual appeal. Prevention of leaks and blockages may be particularly important when only a limited power supply to the reduced pressure source and other components is available. Thus, improvements to dressings, systems, and methods that enhance the management of fluid extracted from a tissue site for increasing reliability, efficiency, visual appeal, and the useable life of the dressing and system are desirable.

SUMMARY

Shortcomings with certain aspects of tissue treatment systems, apparatus, and methods are addressed as shown and described in a variety of illustrative, non-limiting embodiments herein.

In some embodiments, a system for treating a tissue site may include a tissue interface, a dressing, a reduced-pressure source, a therapy unit, and a multi-lumen conduit. The tissue interface may be adapted to be positioned proximate to the tissue site. The dressing may include a sealing member and a conduit interface. The sealing member may be adapted to cover the tissue interface and the tissue site to provide a sealed space between the sealing member and the tissue site. The conduit interface may be positioned proximate to the sealing member and in fluid communication with the tissue interface. The reduced-pressure source may be adapted to provide a reduced pressure to the dressing. The therapy unit may be configured to receive a reduced-pressure feedback signal from the dressing. The multi-lumen conduit may comprise a wall carrying a primary lumen and at least one secondary lumen. The primary lumen may be in fluid communication between the dressing and the reduced-pressure source, and the at least one secondary lumen may be in fluid communication between the dressing and the therapy unit. At least a portion of the wall of the multi-lumen conduit may be comprised of an absorbent material that is vapor permeable and liquid impermeable.

In other embodiments, a multi-lumen conduit for treating a tissue site with reduced pressure may include a wall, a primary lumen, and at least one secondary lumen. The wall may include a first wall material and a second wall material. The first wall material may comprise a substantially non-absorbent material that is vapor impermeable and liquid impermeable. The second wall material may comprise an absorbent material that is vapor permeable and liquid impermeable. The primary lumen and the at least one secondary lumen may be carried by the wall. The second wall material may be positioned in fluid contact with the at least one secondary lumen.

Other aspects, features, and advantages of the illustrative embodiments will become apparent with reference to the drawings and detailed description that follow.

BRIEF DESCRIPTION OF THE DRAWINGS

FIG. 2 is a cut-away view of the dressing of FIG. 1;

FIG. 3 is detail view taken at reference FIG. 3, depicted in FIG. 1, illustrating the dressing of FIG. 1 positioned proximate to tissue surrounding the tissue site;

FIG. 5 is a cut-away view of an illustrative embodiment of a fluid management assembly according to the dressing and system of FIG. 1;

FIG. 6 is a cut-away view of another illustrative embodiment of a fluid management assembly according to the dressing and system of FIG. 1;

FIG. 9A is a cross-section of an illustrative embodiment of a multi-lumen conduit suitable for use with the dressing and system of FIG. 1;

FIG. 9B is a cross-section of another illustrative embodiment of a multi-lumen conduit suitable for use with the dressing and system of FIG. 1;

FIG. 9C is a cross-section of another illustrative embodiment of a multi-lumen conduit suitable for use with the dressing and system of FIG. 1;

DETAILED DESCRIPTION OF ILLUSTRATIVE EMBODIMENTS

In the following detailed description of non-limiting, illustrative embodiments, reference is made to the accompanying drawings that form a part hereof. Other embodiments may be utilized, and logical, structural, mechanical, electrical, and chemical changes may be made without departing from the scope of the appended claims. To avoid detail not necessary to enable those skilled in the art to practice the embodiments described herein, the description may omit certain information known to those skilled in the art. The following detailed description is non-limiting, and the scope of the illustrative embodiments are defined by the appended claims. As used herein, unless otherwise indicated, "or" does not require mutual exclusivity.

Figure 1:
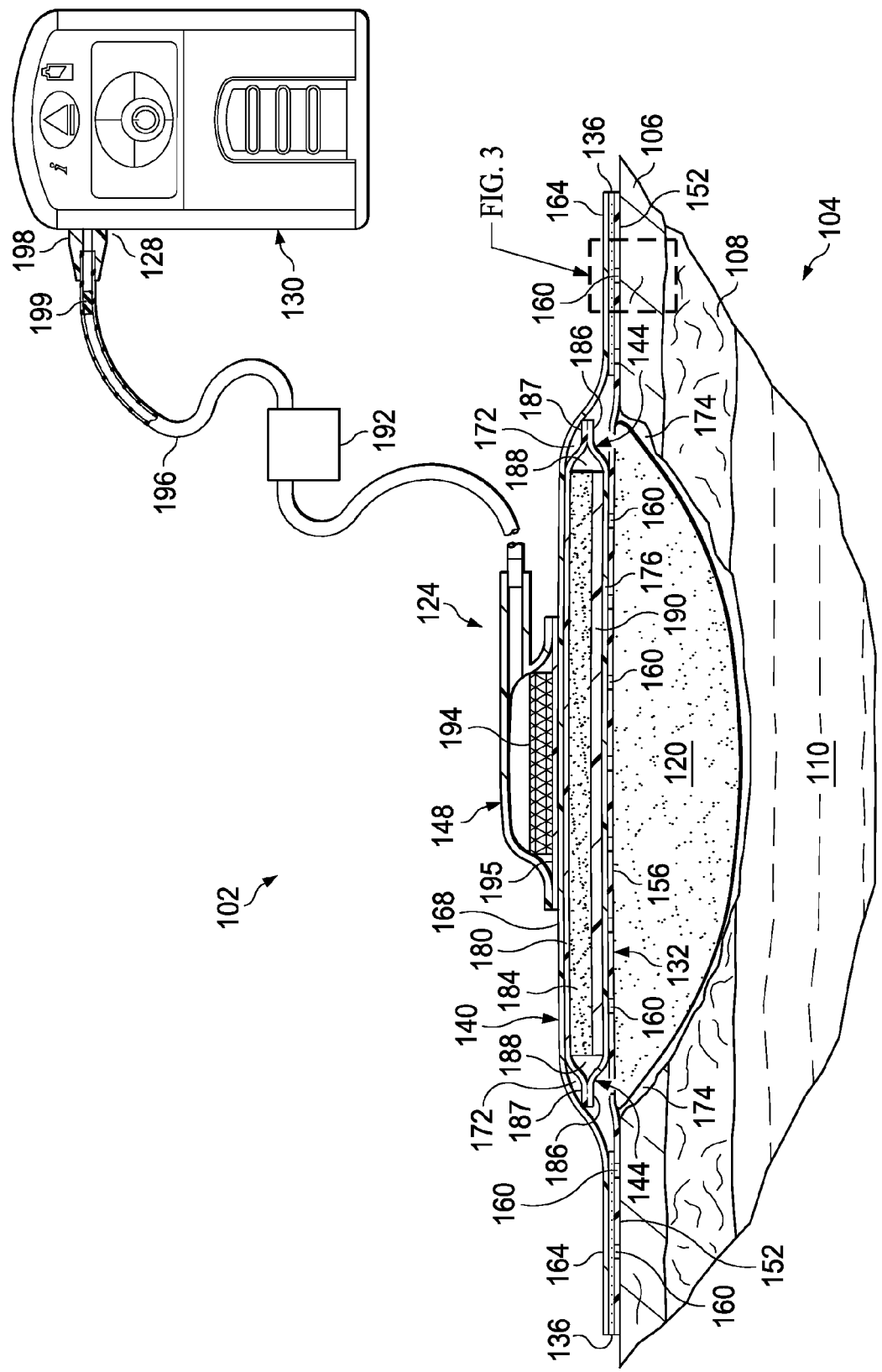
FIG. 1 is a cut-away view of an illustrative embodiment of a system for treating a tissue site depicting an illustrative embodiment of a dressing deployed at a tissue site.

Referring to the drawings, FIG. 1 depicts an embodiment of a system 102 for treating a tissue site 104 of a patient. The tissue site 104 may extend through or otherwise involve an epidermis 106, a dermis 108, and a subcutaneous tissue 110. The tissue site 104 may be a sub-surface tissue site as depicted in FIG. 1 that extends below the surface of the epidermis 106. Further, the tissue site 104 may be a surface tissue site (not shown) that predominantly resides on the surface of the epidermis 106, such as, for example, an incision. The system 102 may provide therapy to, for example, the epidermis 106, the dermis 108, and the subcutaneous tissue 110, regardless of the positioning of the system 102 or the type of tissue site. The system 102 may also be utilized without limitation at other tissue sites.

Further, the tissue site 104 may be the bodily tissue of any human, animal, or other organism, including bone tissue, adipose tissue, muscle tissue, dermal tissue, vascular tissue, connective tissue, cartilage, tendons, ligaments, or any other tissue. Treatment of tissue site 104 may include removal of fluids, e.g., exudate or ascites.

Continuing with FIG. 1, the system 102 may include an optional tissue interface, such as an interface manifold 120. Further, the system 102 may include a dressing 124, and a reduced-pressure source 128. The reduced-pressure source 128 may be a component of an optional therapy unit 130 as shown in FIG. 1. In some embodiments, the reduced-pressure source 128 and the therapy unit 130 may be separate components. As indicated above, the interface manifold 120 is an optional component that may be omitted for different types of tissue sites or different types of therapy using reduced pressure, such as, for example, epithelialization. If equipped, the interface manifold 120 may be adapted to be positioned proximate to or adjacent to the tissue site 104, such as, for example, by cutting or otherwise shaping the interface manifold 120 in any suitable manner to fit the tissue site 104. As described below, the interface manifold 120 may be adapted to be positioned in fluid communication with the tissue site 104 to distribute reduced pressure to the tissue site 104. In some embodiments, the interface manifold 120 may be positioned in direct contact with the tissue site 104. The tissue interface or the interface manifold 120 may be formed from any manifold material or flexible bolster material that provides a vacuum space, or treatment space, such as, for example, a porous and permeable foam or foam-like material, a member formed with pathways, a graft, or a gauze. As a more specific, non-limiting example, the interface manifold 120 may be a reticulated, open-cell polyurethane or polyether foam that allows good permeability of fluids while under a reduced pressure. One such foam material is the VAC® GranuFoam® material available from Kinetic Concepts, Inc. (KCI) of San Antonio, Tex. Any material or combination of materials may be used as a manifold material for the interface manifold 120 provided that the manifold material is operable to distribute or collect fluid. For example, herein the term manifold may refer to a substance or structure that is provided to assist in delivering fluids to or removing fluids from a tissue site through a plurality of pores, pathways, or flow channels. The plurality of pores, pathways, or flow channels may be interconnected to improve distribution of fluids provided to and removed from an area around the manifold. Examples of manifolds may include, without limitation, devices that have structural elements arranged to form flow channels, cellular foam, such as open-cell foam, porous tissue collections, and liquids, gels, and foams that include or cure to include flow channels.

A material with a higher or lower density than GranuFoam® material may be desirable for the interface manifold 120 depending on the application. Among the many possible materials, the following may be used: GranuFoam® material, Foamex® technical foam (www.foamex.com), a molded bed of nails structures, a patterned grid material such as those manufactured by Sercol Industrial Fabrics, 3D textiles such as those manufactured by Baltex of Derby, U.K., a gauze, a flexible channel-containing member, a graft, etc. In some instances, ionic silver may be added to the interface manifold 120 by, for example, a micro bonding process. Other substances, such as anti-microbial agents, may be added to the interface manifold 120 as well.

In some embodiments, the interface manifold 120 may comprise a porous, hydrophobic material. The hydrophobic characteristics of the interface manifold 120 may prevent the interface manifold 120 from directly absorbing fluid, such as exudate, from the tissue site 104, but allow the fluid to pass through.

Continuing with FIG. 1, the dressing 124 may be adapted to provide reduced pressure from the reduced-pressure source 128 to the interface manifold 120, and to store fluid extracted from the tissue site 104 through the interface manifold 120. The dressing 124 may include a base layer 132, an adhesive 136, a sealing member 140, a fluid management assembly 144, and a conduit interface 148. Components of the dressing 124 may be added or removed to suit a particular application.

Referring to FIGS. 1-4B, the base layer 132 may have a periphery 152 surrounding a central portion 156, and a plurality of apertures 160 disposed through the periphery 152 and the central portion 156. The base layer 132 may also have corners 158 and edges 159. The corners 158 and the edges 159 may be part of the periphery 152. One of the edges 159 may meet another of the edges 159 to define one of the corners 158. Further, the base layer 132 may have a border 161 substantially surrounding the central portion 156 and positioned between the central portion 156 and the periphery 152. The border 161 may be free of the apertures 160. The base layer 132 may cover the interface manifold 120 and tissue surrounding the tissue site 104 such that the central portion 156 of the base layer 132 is positioned adjacent to or proximate to the interface manifold 120, and the periphery 152 of the base layer 132 is positioned adjacent to or proximate to tissue surrounding the tissue site 104. In this manner, the periphery 152 of the base layer 132 may surround the interface manifold 120. Further, the apertures 160 in the base layer 132 may be in fluid communication with the interface manifold 120 and tissue surrounding the tissue site 104.

Figure 4A:
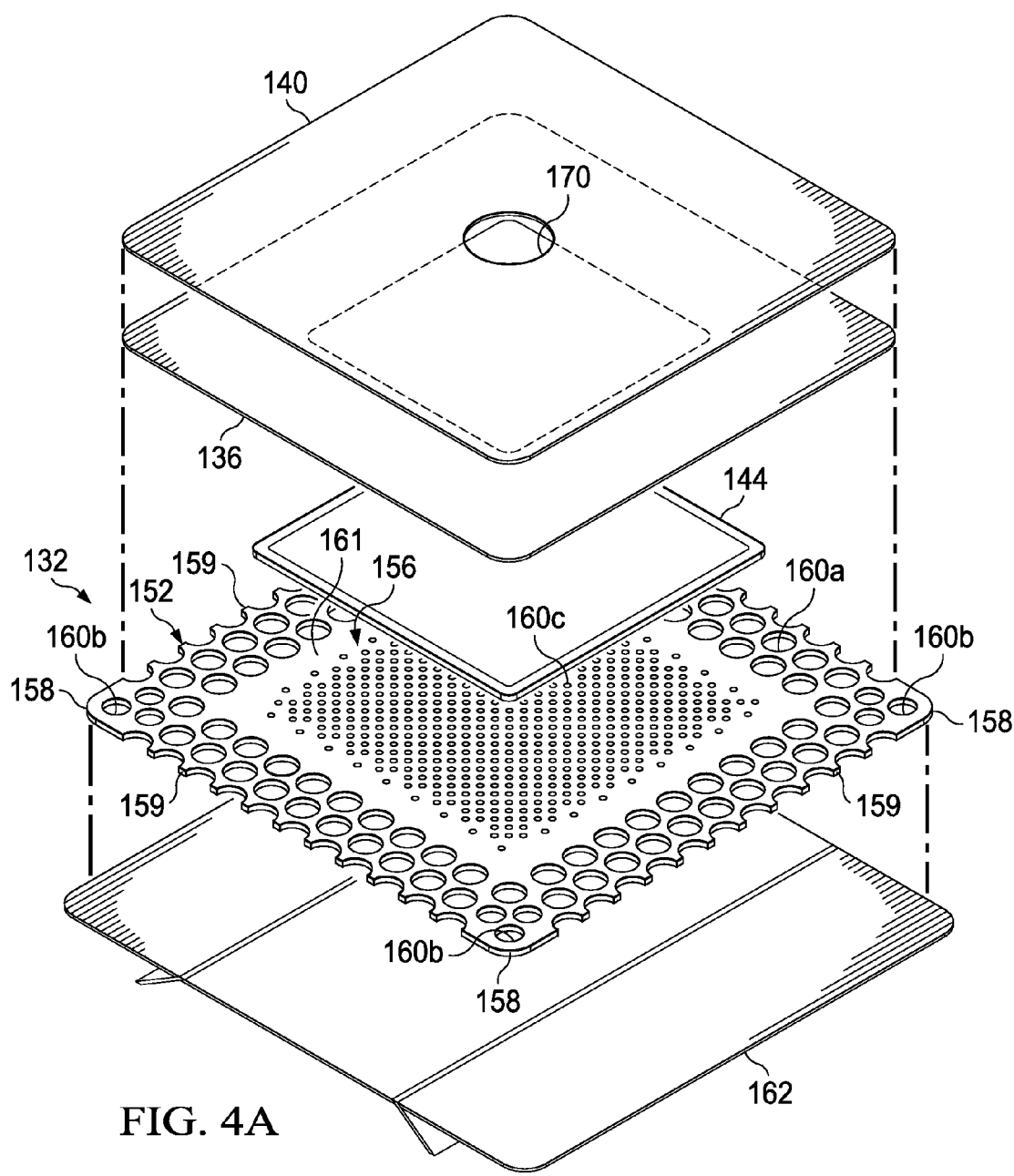
FIG. 4A is an exploded view of the dressing of FIG. 1, depicted without a conduit interface and with an illustrative embodiment of a release liner for protecting the dressing prior to application at a tissue site.
Figure 4B:
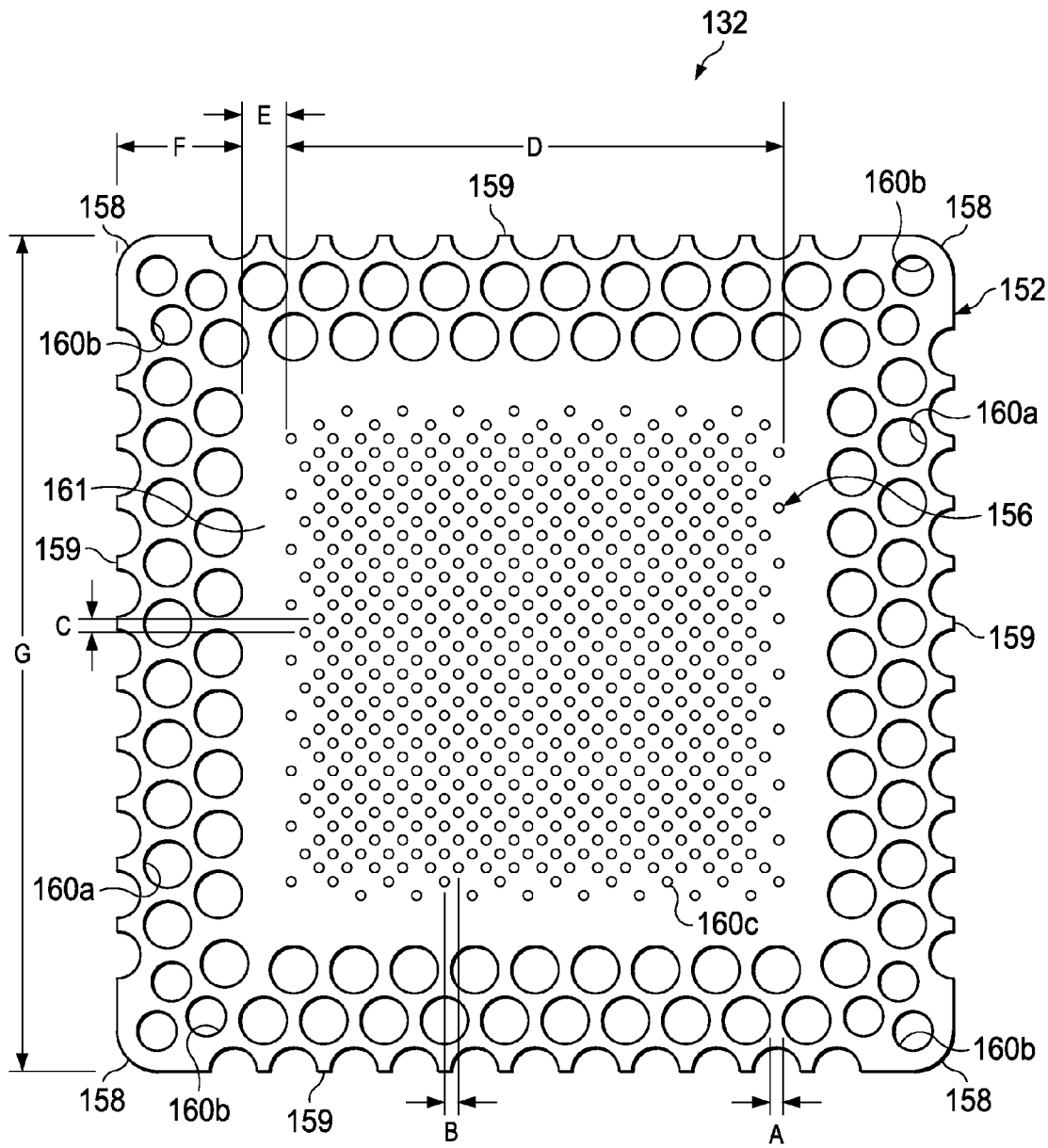
FIG. 4B is a plan view of an illustrative embodiment of a base layer depicted in the dressing of FIG. 4A.

The apertures 160 in the base layer 132 may have any shape, such as, for example, circles, squares, stars, ovals, polygons, slits, complex curves, rectilinear shapes, triangles, or other shapes. The apertures 160 may be formed by cutting, by application of local RF energy, or other suitable techniques for forming an opening. As shown in FIGS. 4A-4B, each of the apertures 160 of the plurality of apertures 160 may be substantially circular in shape, having a diameter and an area. The area of each of the apertures 160 may refer to an open space or open area defining each of the apertures 160. The diameter of each of the apertures 160 may define the area of each of the apertures 160. For example, the area of one of the apertures 160 may be defined by multiplying the square of half the diameter of the aperture 160 by the value 3.14. Thus, the following equation may define the area of one of the apertures 160: Area=3.14*(diameter/2)^2. The area of the apertures 160 described in the illustrative embodiments herein may be substantially similar to the area in other embodiments (not shown) for the apertures 160 that may have non-circular shapes. The diameter of each of the apertures 160 may be substantially the same, or each of the diameters may vary depending, for example, on the position of the aperture 160 in the base layer 132. For example, the diameter of the apertures 160 in the periphery 152 of the base layer 132 may be larger than the diameter of the apertures 160 in the central portion 156 of the base layer 132. Further, the diameter of each of the apertures 160 may be between about 1 millimeter to about 50 millimeters. In some embodiments, the diameter of each of the apertures 160 may be between about 1 millimeter to about 20 millimeters. The apertures 160 may have a uniform pattern or may be randomly distributed on the base layer 132. The size and configuration of the apertures 160 may be designed to control the adherence of the dressing 124 to the epidermis 106 as described below.

Referring to FIGS. 4A-4B, in some embodiments, the apertures 160 positioned in the periphery 152 may be apertures 160a, the apertures 160 positioned at the corners 158 of the periphery 152 may be apertures 160b, and the apertures 160 positioned in the central portion 156 may be apertures 160c. The apertures 160a may have a diameter between about 9.8 millimeters to about 10.2 millimeters. The apertures 160b may have a diameter between about 7.75 millimeters to about 8.75 millimeters. The apertures 160c may have a diameter between about 1.8 millimeters to about 2.2 millimeters. The diameter of each of the apertures 160a may be separated from one another by a distance A between about 2.8 millimeters to about 3.2 millimeters. Further, the diameter of at least one of the apertures 160a may be separated from the diameter of at least one of the apertures 160b by the distance A. The diameter of each of the apertures 160b may also be separated from one another by the distance A. A center of one of the apertures 160c may be separated from a center of another of the apertures 160c in a first direction by a distance B between about 2.8 millimeters to about 3.2 millimeters. In a second direction transverse to the first direction, the center of one of the apertures 160c may be separated from the center of another of the apertures 160c by a distance C between about 2.8 millimeters to about 3.2 millimeters. As shown in FIGS. 4A-4B, the distance B and the distance C may be increased for the apertures 160c in the central portion 156 being positioned proximate to or at the border 161 compared to the apertures 160c positioned away from the border 161.

As shown in FIGS. 4A-4B, the central portion 156 of the base layer 132 may be substantially square with each side of the central portion 156 having a length D between about 100 millimeters to about 108 millimeters. In some embodiments, the length D may be between about 106 millimeters to about 108 millimeters. The border 161 of the base layer 132 may have a width E between about 4 millimeters to about 11 millimeters and may substantially surround the central portion 156 and the apertures 160c in the central portion 156. In some embodiments, the width E may be between about 9 millimeters to about 10 millimeters. The periphery 152 of the base layer 132 may have a width F between about 25 millimeters to about 35 millimeters and may substantially surround the border 161 and the central portion 156. In some embodiments, the width F may be between about 26 millimeters to about 28 millimeters. Further, the periphery 152 may have a substantially square exterior with each side of the exterior having a length G between about 154 millimeters to about 200 millimeters. In some embodiments, the length G may be between about 176 millimeters to about 184 millimeters. Although FIGS. 4A-4B depict the central portion 156, the border 161, and the periphery 152 of the base layer 132 as having a substantially square shape, these and other components of the base layer 132 may have any shape to suit a particular application. Further, the dimensions of the base layer 132 as described herein may be increased or decreased, for example, substantially in proportion to one another to suit a particular application. The use of the dimensions in the proportions described above may enhance the cosmetic appearance of a tissue site. For example, these proportions may provide a surface area for the base layer 132, regardless of shape, that is sufficiently smooth to enhance the movement and proliferation of epithelial cells at the tissue site 104, and reduce the likelihood of granulation tissue in-growth into the dressing 124.

The base layer 132 may be a soft, pliable material suitable for providing a fluid seal with the tissue site 104 as described herein. For example, the base layer 132 may comprise a silicone gel, a soft silicone, hydrocolloid, hydrogel, polyurethane gel, polyolefin gel, hydrogenated styrenic copolymer gels, a foamed gel, a soft closed cell foam such as polyurethanes and polyolefins coated with an adhesive described below, polyurethane, polyolefin, or hydrogenated styrenic copolymers. The base layer 132 may have a thickness between about 500 microns (μm) and about 1000 microns (μm). In some embodiments, the base layer 132 has a stiffness between about 5 Shore OO and about 80 Shore OO. The base layer 132 may be comprised of hydrophobic or hydrophilic materials.

In some embodiments (not shown), the base layer 132 may be a hydrophobic-coated material. For example, the base layer 132 may be formed by coating a spaced material, such as, for example, woven, nonwoven, molded, or extruded mesh with a hydrophobic material. The hydrophobic material for the coating may be a soft silicone, for example. In this manner, the adhesive 136 may extend through openings in the spaced material analogous to the apertures 160 described below.

The adhesive 136 may be in fluid communication with the apertures 160 in at least the periphery 152 of the base layer 132. In this manner, the adhesive 136 may be in fluid communication with the tissue surrounding the tissue site 104 through the apertures 160 in the base layer 132. As described below and shown in FIG. 3, the adhesive 136 may extend or be pressed through the plurality of apertures 160 to contact the epidermis 106 for securing the dressing 124 to, for example, the tissue surrounding the tissue site 104. The apertures 160 may provide sufficient contact of the adhesive 136 to the epidermis 106 to secure the dressing 124 about the tissue site 104. However, the configuration of the apertures 160 and the adhesive 136, described below, may permit release and repositioning of the dressing 124 about the tissue site 104.

At least one of the apertures 160a in the periphery 152 of the base layer 132 may be positioned at the edges 159 of the periphery 152 and may have an interior cut open or exposed at the edges 159 that is in fluid communication in a lateral direction with the edges 159. The lateral direction may refer to a direction toward the edges 159 and in the same plane as the base layer 132. As shown in FIGS. 4A-4B, a plurality of the apertures 160a in the periphery 152 may be positioned proximate to or at the edges 159 and in fluid communication in a lateral direction with the edges 159. The apertures 160a positioned proximate to or at the edges 159 may be spaced substantially equidistant around the periphery 152 as shown in FIGS. 4A-4B. However, in some embodiments, the spacing of the apertures 160a proximate to or at the edges 159 may be irregular. The adhesive 136 may be in fluid communication with the edges 159 through the apertures 160a being exposed at the edges 159. In this manner, the apertures 160a at the edges 159 may permit the adhesive 136 to flow around the edges 159 for enhancing the adhesion of the edges 159 around the tissue site 104, for example.

Continuing with FIGS. 4A-4B, the apertures 160b at the corners 158 of the periphery 152 may be smaller than the apertures 160a in other portions of the periphery 152 as described above. For a given geometry of the corners 158, the smaller size of the apertures 160b compared to the apertures 160a may maximize the surface area of the adhesive 136 exposed and in fluid communication through the apertures 160b at the corners 158. For example, as shown in FIGS. 4A-4B, the edges 159 may intersect at substantially a right angle, or about 90 degrees, to define the corners 158. Also as shown, the corners 158 may have a radius of about 10 millimeters. Three of the apertures 160b having a diameter between about 7.75 millimeters to about 8.75 millimeters may be positioned in a triangular configuration at the corners 158 to maximize the exposed surface area for the adhesive 136. The size and number of the apertures 160b in the corners 158 may be adjusted as necessary, depending on the chosen geometry of the corners 158, to maximize the exposed surface area of the adhesive 136 as described above. Further, the apertures 160b at the corners 158 may be fully housed within the base layer 132, substantially precluding fluid communication in a lateral direction exterior to the corners 158. The apertures 160b at the corners 158 being fully housed within the base layer 132 may substantially preclude fluid communication of the adhesive 136 exterior to the corners 159, and may provide improved handling of the dressing 124 during deployment at the tissue site 104. Further, the exterior of the corners 158 being substantially free of the adhesive 136 may increase the flexibility of the corners 158 to enhance comfort.

Similar to the apertures 160b in the corners 158, any of the apertures 160 may be adjusted in size and number to maximize the surface area of the adhesive 136 in fluid communication through the apertures 160 for a particular application or geometry of the base layer 132. For example, in some embodiments (not shown) the apertures 160b, or apertures of another size, may be positioned in the periphery 152 and at the border 161. Similarly, the apertures 160b, or apertures of another size, may be positioned as described above in other locations of the base layer 132 that may have a complex geometry or shape.

The adhesive 136 may be a medically-acceptable adhesive. The adhesive 136 may also be flowable. For example, the adhesive 136 may comprise an acrylic adhesive, rubber adhesive, high-tack silicone adhesive, polyurethane, or other adhesive substance. In some embodiments, the adhesive 136 may be a pressure-sensitive adhesive comprising an acrylic adhesive with coating weight of 15 grams/m$^2$ (gsm) to 70 grams/m$^2$ (gsm). The adhesive 136 may be a layer having substantially the same shape as the periphery 152 of the base layer 132 as shown in FIG. 4A. In some embodiments, the layer of the adhesive 136 may be continuous or discontinuous. Discontinuities in the adhesive 136 may be provided by apertures (not shown) in the adhesive 136. The apertures in the adhesive 136 may be formed after application of the adhesive 136 or by coating the adhesive 136 in patterns on a carrier layer, such as, for example, a side of the sealing member 140 adapted to face the epidermis 106. Further, the apertures in the adhesive 136 may be sized to control the amount of the adhesive 136 extending through the apertures 160 in the base layer 132 to reach the epidermis 106. The apertures in the adhesive 136 may also be sized to enhance the Moisture Vapor Transfer Rate (MVTR) of the dressing 124, described further below.

Factors that may be utilized to control the adhesion strength of the dressing 124 may include the diameter and number of the apertures 160 in the base layer 132, the thickness of the base layer 132, the thickness and amount of the adhesive 136, and the tackiness of the adhesive 136. An increase in the amount of the adhesive 136 extending through the apertures 160 generally corresponds to an increase in the adhesion strength of the dressing 124. A decrease in the thickness of the base layer 132 generally corresponds to an increase in the amount of adhesive 136 extending through the apertures 160. Thus, the diameter and configuration of the apertures 160, the thickness of the base layer 132, and the amount and tackiness of the adhesive utilized may be varied to provide a desired adhesion strength for the dressing 124. For example, the thickness of the base layer 132 may be about 200 microns, the adhesive layer 136 may have a thickness of about 30 microns and a tackiness of 2000 grams per 25 centimeter wide strip, and the diameter of the apertures 160a in the base layer 132 may be about 10 millimeters.

In some embodiments, the tackiness of the adhesive 136 may vary in different locations of the base layer 132. For example, in locations of the base layer 132 where the apertures 160 are comparatively large, such as the apertures 160a, the adhesive 136 may have a lower tackiness than other locations of the base layer 132 where the apertures 160 are smaller, such as the apertures 160b and 160c. In this manner, locations of the base layer 132 having larger apertures 160 and lower tackiness adhesive 136 may have an adhesion strength comparable to locations having smaller apertures 160 and higher tackiness adhesive 136.

Clinical studies have shown that the configuration described herein for the base layer 132 and the adhesive 136 may reduce the occurrence of blistering, erythema, and leakage when in use. Such a configuration may provide, for example, increased patient comfort and increased durability of the dressing 124.

Referring to the embodiment of FIG. 4B, a release liner 162 may be attached to or positioned adjacent to the base layer 132 to protect the adhesive 136 prior to application of the dressing 124 to the tissue site 104. Prior to application of the dressing 124 to the tissue site 104, the base layer 132 may be positioned between the sealing member 140 and the release liner 162. Removal of the release liner 162 may expose the base layer 132 and the adhesive 136 for application of the dressing 124 to the tissue site 104. The release liner 162 may also provide stiffness to assist with, for example, deployment of the dressing 124. The release liner 162 may be, for example, a casting paper, a film, or polyethylene. Further, the release liner 162 may be a polyester material such as polyethylene terephthalate (PET), or similar polar semi-crystalline polymer. The use of a polar semi-crystalline polymer for the release liner 162 may substantially preclude wrinkling or other deformation of the dressing 124. For example, the polar semi-crystalline polymer may be highly orientated and resistant to softening, swelling, or other deformation that may occur when brought into contact with components of the dressing 124, or when subjected to temperature or environmental variations, or sterilization. Further, a release agent may be disposed on a side of the release liner 162 that is configured to contact the base layer 132. For example, the release agent may be a silicone coating and may have a release factor suitable to facilitate removal of the release liner 162 by hand and without damaging or deforming the dressing 124. In some embodiments, the release agent may be fluorosilicone. In other embodiments, the release liner 162 may be uncoated or otherwise used without a release agent.

Continuing with FIGS. 1-4B, the sealing member 140 has a periphery 164 and a central portion 168. The sealing member 140 may additionally include an aperture 170, as described below. The periphery 164 of the sealing member 140 may be positioned proximate to the periphery 152 of the base layer 132 such that the central portion 168 of the sealing member 140 and the central portion 156 of the base layer 132 define an enclosure 172. The adhesive 136 may be positioned at least between the periphery 164 of the sealing member 140 and the periphery 152 of the base layer 132. The sealing member 140 may cover the tissue site 104 and the interface manifold 120 to provide a fluid seal and a sealed space 174 between the tissue site 104 and the sealing member 140 of the dressing 124. Further, the sealing member 140 may cover other tissue, such as a portion of the epidermis 106, surrounding the tissue site 104 to provide the fluid seal between the sealing member 140 and the tissue site 104. In some embodiments, a portion of the periphery 164 of the sealing member 140 may extend beyond the periphery 152 of the base layer 132 and into direct contact with tissue surrounding the tissue site 104. In other embodiments, the periphery 164 of the sealing member 140, for example, may be positioned in contact with tissue surrounding the tissue site 104 to provide the sealed space 174 without the base layer 132. Thus, the adhesive 136 may also be positioned at least between the periphery 164 of the sealing member 140 and tissue, such as the epidermis 106, surrounding the tissue site 104. The adhesive 136 may be disposed on a surface of the sealing member 140 adapted to face the tissue site 104 and the base layer 132.

The sealing member 140 may be formed from any material that allows for a fluid seal. A fluid seal is a seal adequate to maintain reduced pressure at a desired site given the particular reduced pressure source or system involved. The sealing member 140 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Expopack Advanced Coatings of Wrexham, United Kingdom having, for example, an MVTR (inverted cup technique) of 14400 g/m²/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Pasadena, Calif.; polyether block polyamide copolymer (PEBAX), for example, from Arkema, France; Expopack 2327; or other appropriate material.

The sealing member 140 may be vapor permeable and liquid impermeable, thereby allowing vapor and inhibiting liquids from exiting the sealed space 174 provided by the dressing 124. In some embodiments, the sealing member 140 may be a flexible, breathable film, membrane, or sheet having a high MVTR of, for example, at least about 300 g/m² per 24 hours. In other embodiments, a low or no vapor transfer drape might be used. The sealing member 140 may comprise a range of medically suitable films having a thickness between about 15 microns (μm) to about 50 microns (μm).

The fluid management assembly 144 may be disposed in the enclosure 172 and may include a first wicking layer 176, a second wicking layer 180, and an absorbent layer 184. The absorbent layer 184 may be positioned in fluid communication between the first wicking layer 176 and the second wicking layer 180. The first wicking layer 176 may have a grain structure (not shown) adapted to wick fluid along a surface of the first wicking layer 176. Similarly, the second wicking layer 180 may have a grain structure (not shown) adapted to wick fluid along a surface of the second wicking layer 180. For example, the first wicking layer 176 and the second wicking layer 180 may wick or otherwise transport fluid in a lateral direction along the surfaces of the first wicking layer 176 and the second wicking layer 180, respectively. The surfaces of the first wicking layer 176 and the second wicking layer 180 may be normal relative to the thickness of each of the first wicking layer 176 and the second wicking layer 180. The wicking of fluid along the first wicking layer 176 and the second wicking layer 180 may enhance the distribution of the fluid over a surface area of the absorbent layer 184 that may increase absorbent efficiency and resist fluid blockages. Fluid blockages may be caused by, for example, fluid pooling in a particular location in the absorbent layer 184 rather than being distributed more uniformly across the absorbent layer 184. The laminate combination of the first wicking layer 176, the second wicking layer 180, and the absorbent layer 184 may be adapted as described above to maintain an open structure, resistant to blockage, capable of maintaining fluid communication with, for example, the tissue site 104.

Referring to the embodiments of the fluid management assembly 144 depicted in FIGS. 1, 2, 5, and 6, a peripheral portion 186 of the first wicking layer 176 may be coupled to a peripheral portion 187 of the second wicking layer 180 to define a wicking layer enclosure 188 between the first wicking layer 176 and the second wicking layer 180. In some exemplary embodiments, the wicking layer enclosure 188 may surround or otherwise encapsulate the absorbent layer 184 between the first wicking layer 176 and the second wicking layer 180.

Referring specifically to FIGS. 5 and 6, the fluid management assembly 144 may include, without limitation, any number of wicking layers and absorbent layers as desired for treating a particular tissue site. For example, the absorbent layer 184 may be a plurality of absorbent layers 184 positioned in fluid communication between the first wicking layer 176 and the second wicking layer 180 as described above. Further, as depicted in FIG. 6, at least one intermediate wicking layer 189 may be disposed in fluid communication between the plurality of absorbent layers 184. Similar to the absorbent layer 184 described above, the plurality of absorbent layers 184 and the at least one intermediate wicking layer 189 may be positioned within the wicking layer enclosure 188. In some embodiments, the absorbent layer 184 may be disposed between the sealing member 140 and the interface manifold 120, and the first wicking layer 176 and the second wicking layer 180 may be omitted.

In the embodiments of FIGS. 5 and 6, sides 184a of the absorbent layers 184 may remain in fluid communication with one another for enhancing efficiency. Similarly, in the embodiment of FIG. 6, sides 189a of the at least one intermediate wicking layer 189 may remain in fluid communication with one another and with the sides 184a of the absorbent layers 184. Further, including additional absorbent layers 184 may increase the absorbent mass of the fluid management assembly 144 and generally provide greater fluid capacity. However, for a given absorbent mass, multiple light coat-weight absorbent layers 184 may be utilized rather than a single heavy coat-weight absorbent layer 184 to provide a greater absorbent surface area for further enhancing the absorbent efficiency.

In some embodiments, the absorbent layer 184 may be a hydrophilic material adapted to absorb fluid from, for example, the tissue site 104. Materials suitable for the absorbent layer 184 may include Luquafleece® material, Texsus FP2326, BASF 402C, Technical Absorbents 2317 available from Technical Absorbents (www.techabsorbents.com), sodium polyacrylate super absorbers, cellulosics (carboxy methyl cellulose and salts such as sodium CMC), or alginates. Materials suitable for the first wicking layer 176 and the second wicking layer 180 may include any material having a grain structure capable of wicking fluid as described herein, such as, for example, Libeltex TDL2 80 gsm.

The fluid management assembly 144 may be a pre-laminated structure manufactured at a single location or individual layers of material stacked upon one another as described above. Individual layers of the fluid management assembly 144 may be bonded or otherwise secured to one another without adversely affecting fluid management by, for example, utilizing a solvent or non-solvent adhesive, or by thermal welding. Further, the fluid management assembly 144 may be coupled to the border 161 of the base layer 132 in any suitable manner, such as, for example, by a weld or an adhesive. The border 161 being free of the apertures 160 as described above may provide a flexible barrier between the fluid management assembly 144 and the tissue site 104 for enhancing comfort.

In some embodiments, the enclosure 172 defined by the base layer 132 and the sealing member 140 may include an anti-microbial layer 190. The addition of the anti-microbial layer 190 may reduce the probability of excessive bacterial growth within the dressing 124 to permit the dressing 124 to remain in place for an extended period. The anti-microbial layer 190 may be, for example, an additional layer included as a part of the fluid management assembly 144 as depicted in FIGS. 1 and 2, or a coating of an anti-microbial agent disposed in any suitable location within the dressing 124. The anti-microbial layer 190 may be comprised of elemental silver or similar compound, for example. In some embodiments, the anti-microbial agent may be formulated in any suitable manner into other components of the dressing 124.

Figure 7:
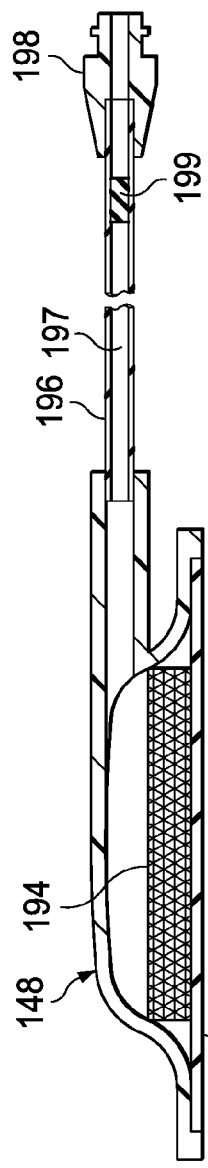
FIG. 7 is a cut-away view of an illustrative embodiment of a conduit interface depicted in the dressing of FIG. 1.

Referring to FIGS. 1, 2, and 7, the conduit interface 148 may be positioned proximate to the sealing member 140 and in fluid communication with the dressing 124 through the aperture 170 in the sealing member 140 to provide reduced pressure from the reduced-pressure source 128 to the dressing 124. Specifically, the conduit interface 148 may be positioned in fluid communication with the enclosure 172 of the dressing 124. The conduit interface 148 may also be positioned in fluid communication with the optional interface manifold 120. As shown, an optional liquid trap 192 may be positioned in fluid communication between the dressing 124 and the reduced-pressure source 128. The liquid trap 192 may be any suitable containment device having a sealed internal volume capable of retaining liquid, such as condensate or other liquids, as described below.

The conduit interface 148 may comprise a medical-grade, soft polymer or other pliable material. As non-limiting examples, the conduit interface 148 may be formed from polyurethane, polyethylene, polyvinyl chloride (PVC), fluorosilicone, or ethylene-propylene, etc. In some illustrative, non-limiting embodiments, conduit interface 148 may be molded from DEHP-free PVC. The conduit interface 148 may be formed in any suitable manner such as by molding, casting, machining, or extruding. Further, the conduit interface 148 may be formed as an integral unit or as individual components and may be coupled to the dressing 124 by, for example, adhesive or welding.

In some embodiments, the conduit interface 148 may be formed of an absorbent material having absorbent and evaporative properties. The absorbent material may be vapor permeable and liquid impermeable, thereby being configured to permit vapor to be absorbed into and evaporated from the material through permeation while inhibiting permeation of liquids. The absorbent material may be, for example, a hydrophilic polymer such as a hydrophilic polyurethane. Although the term hydrophilic polymer may be used in the illustrative embodiments that follow, any absorbent material having the properties described herein may be suitable for use in the system 102. Further, the absorbent material or hydrophilic polymer may be suitable for use in various components of the system 102 as described herein.

The use of such a hydrophilic polymer for the conduit interface 148 may permit liquids in the conduit interface 148 to evaporate, or otherwise dissipate, during operation. For example, the hydrophilic polymer may allow the liquid to permeate or pass through the conduit interface 148 as vapor, in a gaseous phase, and evaporate into the atmosphere external to the conduit interface 148. Such liquids may be, for example, condensate or other liquids. Condensate may form, for example, as a result of a decrease in temperature within the conduit interface 148, or other components of the system 102, relative to the temperature at the tissue site 104. Removal or dissipation of liquids from the conduit interface 148 may increase visual appeal and prevent odor. Further, such removal of liquids may also increase efficiency and reliability by reducing blockages and other interference with the components of the system 102.

Similar to the conduit interface 148, the liquid trap 192, and other components of the system 102 described herein, may also be formed of an absorbent material or a hydrophilic polymer. The absorptive and evaporative properties of the hydrophilic polymer may also facilitate removal and dissipation of liquids residing in the liquid trap 192, and other components of the system 102, by evaporation. Such evaporation may leave behind a substantially solid or gel-like waste. The substantially solid or gel-like waste may be cheaper to dispose than liquids, providing a cost savings for operation of the system 102. The hydrophilic polymer may be used for other components in the system 102 where the management of liquids is beneficial.

In some embodiments, the absorbent material or hydrophilic polymer may have an absorbent capacity in a saturated state that is substantially equivalent to the mass of the hydrophilic polymer in an unsaturated state. The hydrophilic polymer may be fully saturated with vapor in the saturated state and substantially free of vapor in the unsaturated state. In both the saturated state and the unsaturated state, the hydrophilic polymer may retain substantially the same physical, mechanical, and structural properties. For example, the hydrophilic polymer may have a hardness in the unsaturated state that is substantially the same as a hardness of the hydrophilic polymer in the saturated state. The hydrophilic polymer and the components of the system 102 incorporating the hydrophilic polymer may also have a size that is substantially the same in both the unsaturated state and the saturated state. Further, the hydrophilic polymer may remain dry, cool to the touch, and pneumatically sealed in the saturated state and the unsaturated state. The hydrophilic polymer may also remain substantially the same color in the saturated state and the unsaturated state. In this manner, this hydrophilic polymer may retain sufficient strength and other physical properties to remain suitable for use in the system 102. An example of such a hydrophilic polymer is offered under the trade name Techophilic HP-93A-100, available from The Lubrizol Corporation of Wickliffe, Ohio, United States. Techophilic HP-93A-100 is an absorbent hydrophilic thermoplastic polyurethane capable of absorbing 100% of the unsaturated mass of the polyurethane in water and having a durometer or Shore Hardness of about 83 Shore A.

The conduit interface 148 may carry an odor filter 194 adapted to substantially preclude the passage of odors from the tissue site 104 out of the sealed space 174. Further, the conduit interface 148 may carry a primary hydrophobic filter 195 adapted to substantially preclude the passage of liquids out of the sealed space 174. The odor filter 194 and the primary hydrophobic filter 195 may be disposed in the conduit interface 148 or other suitable location such that fluid communication between the reduced-pressure source 128, or optional therapy unit 130, and the dressing 124 is provided through the odor filter 194 and the primary hydrophobic filter 195. In some embodiments, the odor filter 194 and the primary hydrophobic filter 195 may be secured within the conduit interface 148 in any suitable manner, such as by adhesive or welding. In other embodiments, the odor filter 194 and the primary hydrophobic filter 195 may be positioned in any exit location in the dressing 124 that is in fluid communication with the atmosphere, the reduced-pressure source 128, or the optional therapy unit 130. The odor filter 194 may also be positioned in any suitable location in the system 102 that is in fluid communication with the tissue site 104.

The odor filter 194 may be comprised of a carbon material in the form of a layer or particulate. For example, the odor filter 194 may comprise a woven carbon cloth filter such as those manufactured by Chemviron Carbon, Ltd. of Lancashire, United Kingdom (www.chemvironcarbon.com). The primary hydrophobic filter 195 may be comprised of a material that is liquid impermeable and vapor permeable. For example, the primary hydrophobic filter 195 may comprise a material manufactured under the designation MMT-314 by W.L. Gore & Associates, Inc. of Newark, Del., United States, or similar materials. The primary hydrophobic filter 195 may be provided in the form of a membrane or layer.

Continuing with FIGS. 1, 2, and 7, the reduced-pressure source 128 provides reduced pressure to the dressing 124 and the sealed space 174. The reduced-pressure source 128 may be any suitable device for providing reduced pressure, such as, for example, a vacuum pump, wall suction, hand pump, or other source. As shown in FIG. 1, the reduced-pressure source 128 may be a component of the therapy unit 130. The therapy unit 130 may include control circuitry and sensors, such as a pressure sensor, that may be configured to monitor reduced pressure at the tissue site 104. The therapy unit 130 may also be configured to control the amount of reduced pressure from the reduced-pressure source 128 being applied to the tissue site 104 according to a user input and a reduced-pressure feedback signal received from the tissue site 104.

As used herein, "reduced pressure" generally refers to a pressure less than the ambient pressure at a tissue site being subjected to treatment. Typically, this reduced pressure will be less than the atmospheric pressure. The reduced pressure may also be less than a hydrostatic pressure at a tissue site. Unless otherwise indicated, values of pressure stated herein are gauge pressures. While the amount and nature of reduced pressure applied to a tissue site will typically vary according to the application, the reduced pressure will typically be between −5 mm Hg and −500 mm Hg, and more typically in a therapeutic range between −100 mm Hg and −200 mm Hg.

The reduced pressure delivered may be constant or varied (patterned or random), and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure. An increase in reduced pressure corresponds to a reduction in pressure (more negative relative to ambient pressure) and a decrease in reduced pressure corresponds to an increase in pressure (less negative relative to ambient pressure).

As shown in FIG. 7, a conduit 196 having an internal lumen 197 may be coupled in fluid communication between the reduced-pressure source 128 and the dressing 124. The internal lumen 197 may have an internal diameter between about 0.5 millimeters to about 3.0 millimeters. More specifically, the internal diameter of the internal lumen 197 may be between about 1 millimeter to about 2 millimeters. The conduit interface 148 may be coupled in fluid communication with the dressing 124 and adapted to connect between the conduit 196 and the dressing 124 for providing fluid communication with the reduced-pressure source 128. The conduit interface 148 may be fluidly coupled to the conduit 196 in any suitable manner, such as, for example, by an adhesive, solvent or non-solvent bonding, welding, or interference fit. The aperture 170 in the sealing member 140 may provide fluid communication between the dressing 124 and the conduit interface 148. Specifically, the conduit interface 148 may be in fluid communication with the enclosure 172 or the sealed space 174 through the aperture 170 in the sealing member 140. In some embodiments, the conduit 196 may be inserted into the dressing 124 through the aperture 170 in the sealing member 140 to provide fluid communication with the reduced-pressure source 128 without use of the conduit interface 148. The reduced-pressure source 128 may also be directly coupled in fluid communication with the dressing 124 or the sealing member 140 without use of the conduit 196. The conduit 196 may be, for example, a flexible polymer tube. A distal end of the conduit 196 may include a coupling 198 for attachment to the reduced-pressure source 128.

The conduit 196 may have a secondary hydrophobic filter 199 disposed in the internal lumen 197 such that fluid communication between the reduced-pressure source 128 and the dressing 124 is provided through the secondary hydrophobic filter 199. The secondary hydrophobic filter 199 may be, for example, a porous, sintered polymer cylinder sized to fit the dimensions of the internal lumen 197 to substantially preclude liquid from bypassing the cylinder.

The secondary hydrophobic filter 199 may also be treated with an absorbent material adapted to swell when brought into contact with liquid to block the flow of the liquid. The secondary hydrophobic filter 199 may be positioned at any location within the internal lumen 197. However, positioning the secondary hydrophobic filter 199 within the internal lumen 197 closer toward the reduced-pressure source 128, rather than the dressing 124, may allow a user to detect the presence of liquid in the internal lumen 197.

In some embodiments, the conduit 196 and the coupling 198 may be formed of an absorbent material or a hydrophilic polymer as described above for the conduit interface 148. In this manner, the conduit 196 and the coupling 198 may permit liquids in the conduit 196 and the coupling 198 to evaporate, or otherwise dissipate, as described above for the conduit interface 148. The conduit 196 and the coupling 198 may be, for example, molded from the hydrophilic polymer separately, as individual components, or together as an integral component. Further, a wall of the conduit 196 defining the internal lumen 197 may be extruded from the hydrophilic polymer. The conduit 196 may be less than about 1 meter in length, but may have any length to suit a particular application. More specifically, a length of about 1 foot or 304.8 millimeters may provide enough absorbent and evaporative surface area to suit many applications, and may provide a cost savings compared to longer lengths. If an application requires additional length for the conduit 196, the absorbent hydrophilic polymer may be coupled in fluid communication with a length of conduit formed of a non-absorbent hydrophobic polymer to provide additional cost savings.

Figure 8:
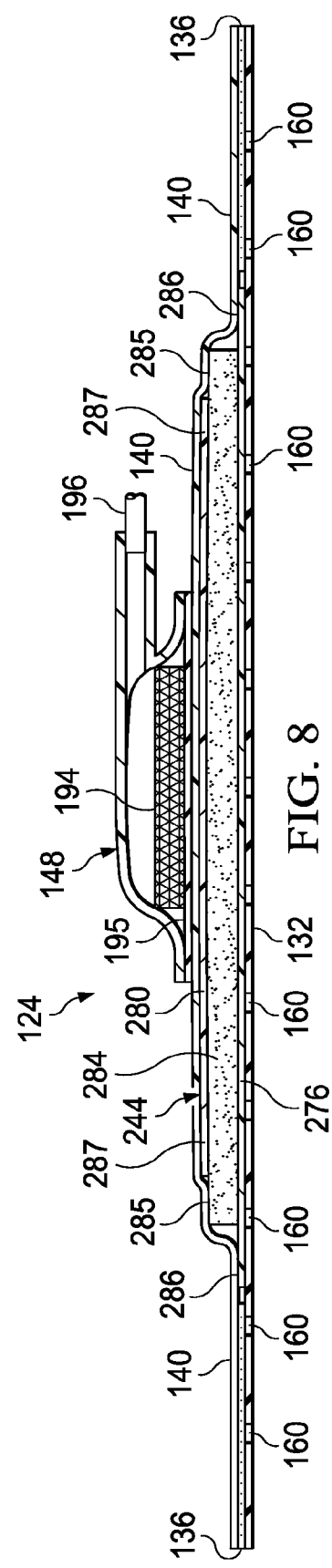
FIG. 8 is a cut-away view of another illustrative embodiment of a fluid management assembly suitable for use with the dressing and system of FIG. 1.

Referring now to FIG. 8, FIG. 8 depicts the dressing 124 including a fluid management assembly 244 suitable for use with the dressing 124 and the system 102. The fluid management assembly 244 may include a first wicking layer 276, a second wicking layer 280, and an absorbent layer 284 comprised of substantially the same materials and properties as those described above in connection with the fluid management assembly 144. Thus, the first wicking layer 276, the second wicking layer 280, and the absorbent layer 284 are analogous to the first wicking layer 176, the second wicking layer 180, and the absorbent layer 184, respectively.

In the fluid management assembly 244, the second wicking layer 280 may have a peripheral portion 287. The second wicking layer 280 and the peripheral portion 287 of the second wicking layer 280 may be positioned in contact with the sealing member 140. The absorbent layer 284 may have a peripheral portion 285 extending beyond the peripheral portion 287 of the second wicking layer 280. The absorbent layer 284 may be positioned adjacent to or proximate to the second wicking layer 280 such that the peripheral portion 285 of the absorbent layer 284 is in contact with the sealing member 140 surrounding the peripheral portion 287 of the second wicking layer 280. Similarly, the first wicking layer 276 may have a peripheral portion 286 extending beyond the peripheral portion 285 of the absorbent layer 284. The first wicking layer 276 may be positioned adjacent to or proximate to the absorbent layer 284 such that the peripheral portion 286 of the first wicking layer 276 is in contact with the sealing member 140 surrounding the peripheral portion 285 of the absorbent layer 284. Further, the first wicking layer 276 may be positioned adjacent to or proximate to the base layer 132. Thus, at least the peripheral portion 287, the peripheral portion 285, and the peripheral portion 286 in contact with the sealing member 140 may be coupled to the sealing member 140, such as, for example, by an adhesive coating disposed on a surface of the sealing member 140 facing the base layer 132. The adhesive coating may be analogous to the adhesive 136 being applied across the surface of the sealing member 140 facing the base layer 132. The second wicking layer 280, the absorbent layer 284, and the first wicking layer 276 may respectively have increasing surface areas to enhance contact with the adhesive coating described above. In other embodiments, the fluid management assembly 244 may include any number of absorbent layers and wicking layers for treating a particular tissue site.

In operation of the system 102 according to some illustrative embodiments, the interface manifold 120 may be disposed against or proximate to the tissue site 104. The dressing 124 may then be applied over the interface manifold 120 and the tissue site 104 to form the sealed space 174. Specifically, the base layer 132 may be applied covering the interface manifold 120 and the tissue surrounding the tissue site 104. The materials described above for the base layer 132 have a tackiness that may hold the dressing 124 initially in position. The tackiness may be such that if an adjustment is desired, the dressing 124 may be removed and reapplied. Once the dressing 124 is in the desired position, a force may be applied, such as by hand pressing, on a side of the sealing member 140 opposite the tissue site 104. The force applied to the sealing member 140 may cause at least some portion of the adhesive 136 to penetrate or extend through the plurality of apertures 160 and into contact with tissue surrounding the tissue site 104, such as the epidermis 106, to releasably adhere the dressing 124 about the tissue site 104. In this manner, the configuration of the dressing 124 described above may provide an effective and reliable seal against challenging anatomical surfaces, such as an elbow or heal, at and around the tissue site 104. Further, the dressing 124 permits re-application or re-positioning to, for example, correct air leaks caused by creases and other discontinuities in the dressing 124 and the tissue site 104. The ability to rectify leaks may increase the reliability of the therapy and reduce power consumption.

As the dressing 124 comes into contact with fluid from the tissue site 104, the fluid moves through the apertures 160 toward the fluid management assembly 144, 244. The fluid management assembly 144, 244 wicks or otherwise moves the fluid through the interface manifold 120 and away from the tissue site 104. As described above, the interface manifold 120 may be adapted to communicate fluid from the tissue site 104 rather than store the fluid. Thus, the fluid management assembly 144, 244 may be more absorbent than the interface manifold 120. The fluid management assembly 144, 244 being more absorbent than the interface manifold 120 provides an absorbent gradient through the dressing 124 that attracts fluid from the tissue site 104 or the interface manifold 120 to the fluid management assembly 144, 244. Thus, in some embodiments, the fluid management assembly 144, 244 may be adapted to wick, pull, draw, or otherwise attract fluid from the tissue site 104 through the interface manifold 120. In the fluid management assembly 144, 244, the fluid initially comes into contact with the first wicking layer 176, 276. The first wicking layer 176, 276 may distribute the fluid laterally along the surface of the first wicking layer 176, 276 as described above for absorption and storage within the absorbent layer 184, 284. Similarly, fluid coming into contact with the second wicking layer 180, 280 may be distributed laterally along the surface of the second wicking layer 180, 280 for absorption within the absorbent layer 184, 284.

Figure 9D:
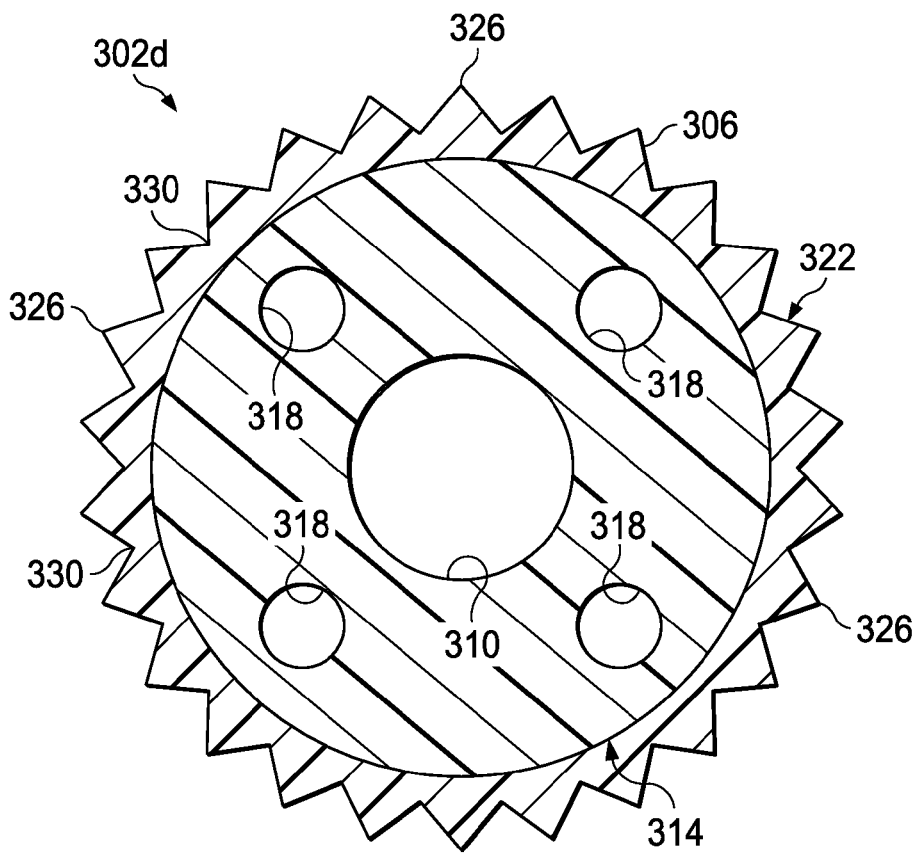
FIG. 9D is a cross-section of another illustrative embodiment of a multi-lumen conduit suitable for use with the dressing and system of FIG. 1.

Referring to FIGS. 9A-9E, in other embodiments, the conduit 196 may be a multi-lumen conduit 302. For example, FIG. 9A depicts an illustrative embodiment of a multi-lumen conduit 302a. The multi-lumen conduit 302a may have an external surface 306, a primary lumen 310, a wall 314, and at least one secondary lumen 318. The wall 314 may carry the primary lumen 310 and the at least one secondary lumen 318. The primary lumen 310 may be substantially isolated from fluid communication with the at least one secondary lumen 318 along the length of the multi-lumen conduit 302a. Although shown in FIG. 9A as having a substantially circular cross-section, the external surface 306 of the multi-lumen conduit 302a may have any shape to suit a particular application. The wall 314 of the multi-lumen conduit 302a may have a thickness between the primary lumen 310 and the external surface 306. As depicted in FIG. 9A, the at least one secondary lumen 318 may be four secondary lumens 318 carried by the wall 314 substantially parallel to the primary lumen 310 and about a perimeter of the primary lumen 310. The secondary lumens 318 may be separate from one another and substantially isolated from fluid communication with one another along the length of the multi-lumen conduit 302a. Further, the secondary lumens 318 may be separate from the primary lumen 310 and substantially isolated from fluid communication with the primary lumen 310. The secondary lumens 318 may also be positioned concentric relative to the primary lumen 310 and substantially equidistant about the perimeter of the primary lumen 310. Although FIG. 9A depicts four secondary lumens 318, any number of secondary lumens 318 may be provided and positioned in any suitable manner for a particular application.

Similar to the internal lumen 197 of the conduit 196, the primary lumen 310 may be coupled in fluid communication between the reduced-pressure source 128 and the dressing 124 as described above. In some embodiments, the primary lumen 310 may be coupled in fluid communication between the conduit interface 148 and the reduced-pressure source 128. Further, analogous to the internal lumen 197, reduced pressure may be provided through the primary lumen 310 from the reduced-pressure source 128 to the dressing 124. In some embodiments, the primary lumen 310 may be configured to extract fluid such as exudate from the tissue site 104. The secondary lumens 318 may be coupled in fluid communication between the therapy unit 130 and the dressing 124. In some embodiments, the at least one secondary lumen 318 may be coupled in fluid communication between the conduit interface 148 and the therapy unit 130. Further, the secondary lumens 318 may be in fluid communication with the primary lumen 310 at the dressing 124 and configured to provide a reduced-pressure feedback signal from the dressing 124 to the therapy unit 130. For example, the secondary lumens 318 may be in fluid communication with the primary lumen 310 at the conduit interface 148 or other component of the dressing 124.

The multi-lumen conduit 302a may be comprised of an absorbent material or hydrophilic polymer, such as, for example, the absorbent material or the hydrophilic polymer described above in connection with the conduit interface 148, the conduit 196, and the coupling 198. The absorbent material or the hydrophilic polymer may be vapor permeable and liquid impermeable. In some embodiments, at least a portion of the wall 314 and the external surface 306 of the multi-lumen conduit 302a may be comprised of the absorbent material or the hydrophilic polymer. In this manner, the multi-lumen conduit 302a may permit liquids, such as condensate, in the multi-lumen conduit 302a to evaporate, or otherwise dissipate, as described above. For example, the absorbent material or the hydrophilic polymer may allow the liquid to pass through the multi-lumen conduit 302a as vapor, in a gaseous phase, and evaporate into the atmosphere external to the multi-lumen conduit 302a. Liquids such as exudate from the tissue site 104 may also be evaporated or dissipated through the multi-lumen conduit 302a in the same manner. This feature may be advantageous when the optional therapy unit 130 is used for monitoring and controlling reduced pressure at the tissue site 104. For example, liquid present in the secondary lumens 318 may interfere with a reduced-pressure feedback signal being transmitted to the therapy unit 130 through the secondary lumens 318. The use of the hydrophilic polymer for the multi-lumen conduit 302a may permit removal of such liquid for enhancing the visual appeal, reliability, and efficiency of the system 102. After evaporation of liquid in the multi-lumen conduit 302a, other blockages from, for example, desiccated exudate, solids, or gel-like substances that were carried by the evaporated liquid may be visible for further remediation. Further, the use of the hydrophilic polymer as described herein may reduce the occurrence of skin damage caused by moisture buildup between components of the system 102, such as the multi-lumen conduit 302a, and the skin of a patient.

Depicted in FIG. 9B is another illustrative embodiment of a multi-lumen conduit 302b. Similar to the multi-lumen conduit 302a, the multi-lumen conduit 302b may have the external surface 306, the primary lumen 310, the wall 314, and the at least one secondary lumen 318 as described above. However, the wall 314 of the multi-lumen conduit 302b may include a first wall material 314a and a second wall material 314b. The first wall material 314a and the second wall material 314b may be comprised of different materials to form the wall 314. For example, the first wall material 314a may comprise a substantially non-absorbent hydrophobic polymer, or other material, that is vapor impermeable and liquid impermeable. The first wall material 314a may completely surround the primary lumen 310, defining the primary lumen 310 as shown in FIG. 9B. In some embodiments (not shown), the first wall material 314a may be positioned around the primary lumen 310 without completely surrounding or defining the primary lumen 310. The second wall material 314b may comprise the same absorbent material or hydrophilic polymer described above for the multi-lumen conduit 302a as being vapor permeable and liquid impermeable. As shown in FIG. 9B, the second wall material 314b may be positioned in fluid contact with the at least one secondary lumen 318. The second wall material 314b may also define the at least one secondary lumen 318 and at least a portion of the external surface 306 of the multi-lumen conduit 302b. In some embodiments (not shown), the second wall material 314b may substantially surround the at least one secondary lumen 318 without completely defining the secondary lumen 318.

Continuing with FIG. 9B, the first wall material 314a may be substantially concentric about the primary lumen 310, and the second wall material 314b may be substantially concentric about and contiguous with the first wall material 314a. The first wall material 314a and the second wall material 314b may be molded, co-extruded, or otherwise combined with one another in any suitable manner to form the wall 314. The wall 314, including the first wall material 314a and the second wall material 314b, may provide a cost savings while retaining the absorbent and evaporative properties of the hydrophilic polymer for remediating liquid in the multi-lumen conduit 302b and the at least one secondary lumen 318. Further, the use of the first wall material 314a as described herein may provide sufficient strength and other physical properties for the multi-lumen conduit 302b to remain serviceable under reduced pressure in the system 102 without regard to the physical properties of second wall material 314b. For example, the use of a non-absorbent hydrophobic polymer for the first wall material 314a may permit the use of absorbent hydrophilic polymers for the second wall material 314b that may not otherwise have sufficient strength for use under reduced pressure in the system 102.

The first wall material 314a may be combined with the second wall material 314b to form the wall 314 in various configurations for remediating liquid in the multi-lumen conduit 302 and the at least one secondary lumen 318. For example, referring to FIG. 9C, depicted is an illustrative embodiment of a multi-lumen conduit 302c. Similar to the multi-lumen conduits 302a and 302b, the multi-lumen conduit 302c may have the external surface 306, the primary lumen 310, the wall 314, and the at least one secondary lumen 318. As shown in FIG. 9C, the wall 314 of the multi-lumen conduit 302c may include the first wall material 314a positioned around the primary lumen 310 and the second wall material 314b disposed in separate portions around each of the secondary lumens 318. In this configuration, for example, the external surface 306 may comprise both the first wall material 314a and the second wall material 314b. Also as shown in FIG. 9C, the first wall material 314a may completely surround the primary lumen 310. The second wall material 314b may be disposed as portions separate from one another and separate from the primary lumen in a radial configuration about the perimeter of the primary lumen 310. However, in some embodiments, the second wall material 314b may be in fluid contact with the primary lumen 310 and may form a portion of the external surface 306. The amount of the second wall material 314b surrounding the secondary lumens 318 may be increased or decreased to suit a particular application depending, for example, on the amount of liquid anticipated to be present and the desired mechanical properties of the multi-lumen conduit 302c.

Continuing with FIG. 9C, the first wall material 314a may have a receptor 320 configured to receive the second wall material 314b. The second wall material 314b surrounding the secondary lumens 318 may have a shape corresponding to the receptor 320 in the first wall material 314a. For example, each portion of the second wall material 314b may have a taper 321a configured to engage a corresponding taper 321b of the receptor 320. The taper 321b may be oriented opposite the taper 321a. As shown in FIG. 9C, the taper 321b of the receptor 320 may taper from the external surface 306 to a smaller dimension toward the primary lumen 310. The taper 321a may have a taper opposite the direction of the taper 321b described above such that the taper 321b is configured to receive and engage the taper 321a.

In some embodiments (not shown), the taper 321a of the second wall material 314b may taper from the external surface 306 to a larger dimension toward the primary lumen 310. The taper 321b of the receptor 320 may have a taper opposite the direction of the taper 321a described above such that the taper 321b is configured to receive and engage the taper 321a. In this configuration, with the taper 321a of the second wall material 314b having a larger dimension toward the primary lumen 310, the opposite taper 321b of the receptor 320 may substantially preclude the second wall material 314b from being pulled away from the receptor 320 in the first wall material 314a. The above embodiments for the tapers 321a and 321b are non-limiting. Other shapes and configurations are suitable for engaging the first wall material 314a with the second wall material 314b, such as, for example, interlocking tabs or other mechanical elements.

The multi-lumen conduit 302 may include other materials and configurations for managing liquid in the multi-lumen conduit 302 as described herein. For example, referring to FIG. 9D, depicted is an illustrative embodiment of a multi-lumen conduit 302d. Similar to the multi-lumen conduits 302a, 302b, and 302c, the multi-lumen conduit 302d may have the external surface 306, the primary lumen 310, the wall 314, and the at least one secondary lumen 318. The multi-lumen conduit 302d may additionally include an external absorbent layer 322. The external absorbent layer 322 may be positioned around the wall 314 of the multi-lumen conduit 302d. The external absorbent layer 322 may be positioned, for example, along the entire length of the multi-lumen conduit 302d or a portion of the length of the multi-lumen conduit 302d. More specifically, the external absorbent layer 322 may be positioned on a portion of the length of the multi-lumen conduit 302d proximate to the dressing 124.

Continuing with FIG. 9D, the wall 314 of the multi-lumen conduit 302d may comprise an absorbent material or a hydrophilic polymer, such as the absorbent material or the hydrophilic polymer described above for the multi-lumen conduit 302a as being vapor permeable and liquid impermeable. Although not shown in FIG. 9D, the wall 314 of the multi-lumen conduit 302d may include the first wall material 314a and the second wall material 314b as described above for FIGS. 9B and 9C. The external absorbent layer 322 may be comprised, for example, of the same absorbent material or hydrophilic polymer of the wall 314. In some embodiments, the external absorbent layer 322 may be comprised of a second absorbent material or a second hydrophilic polymer that is vapor permeable and liquid impermeable. The second absorbent material may have a greater absorbent capacity than the absorbent material or hydrophilic polymer comprising the wall 314 or the second wall material 314b. For example, the second absorbent material of the external absorbent layer 322 may be capable of absorbing more than 100% of the unsaturated mass of the second absorbent material in water. In this manner, the external absorbent layer 322 may be configured to provide an absorptive gradient increasing in absorbent capacity away from the primary lumen 310 and toward the external surface 306. The absorptive gradient may pull, wick, draw, or otherwise attract vapor toward the external surface 306 for evaporation. In some embodiments, the thickness of the wall 314 may be reduced to enhance the passage or permeation of vapor through the wall 314 and to the external atmosphere. In embodiments (not shown) including the first wall material 314a and the second wall material 314b, the external absorbent layer 322 may be positioned at least around the second wall material 314b and in fluid contact with the second wall material 314b.

Continuing with FIG. 9D, the external surface 306 of the multi-lumen conduit 302d may have any shape to suit a particular application. For example, the external surface 306 may have a plurality of protrusions 326 and depressions 330 configured to increase the external surface area of the external surface 306. The increased surface area provided by the protrusions 326 and depressions 330 may enhance the ability of the multi-lumen conduit 302d to evaporate liquids.

Figure 9E:
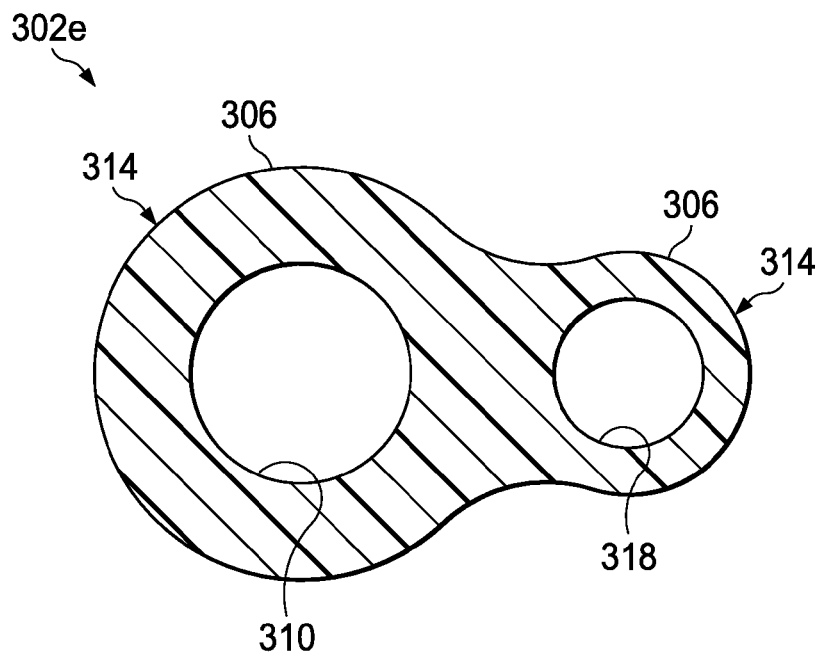
FIG. 9E is a cross-section of another illustrative embodiment of a multi-lumen conduit suitable for use with the dressing and system of FIG. 1.

Referring to FIG. 9E, depicted is an illustrative embodiment of a multi-lumen conduit 302e having an oblong cross section. Similar to the multi-lumen conduits 302a, 302b, 302c, and 302d, the multi-lumen conduit 302e may have the external surface 306, the primary lumen 310, the wall 314, and the at least one secondary lumen 318. However, FIG. 9E depicts the at least one secondary lumen 318 of the multi-lumen conduit 302e as a single secondary lumen 318 that may be carried by the wall 314 beside the primary lumen 310. Such a configuration may provide a substantially flat, low profile shape that may enhance user comfort and may increase the flexibility of the multi-lumen conduit 302e. For example, in this configuration, the multi-lumen conduit 302e may be routed through tight spaces with reduced risk of kinking or blockages of fluid communication. Although not depicted, additional lumens may be added in this substantially flat configuration, laterally disposed from the primary lumen 310 and the secondary lumen 318, as necessary to suit a particular application.

The above features described in connection with the multi-lumen conduits 302a, 302b, 302c, 302d, and 302e may be used in combination with one another to suit a particular application. For example, the external absorbent layer 322 described in the multi-lumen conduit 302d may be used in combination with any of the multi-lumen conduits 302a, 302b, 302c, and 302e. Further, any of the multi-lumen conduits 302a, 302b, 302c, 302d, and 302e may be used with padding (not shown) disposed around the external surface 306, proximate to the dressing 124, for example, to enhance user comfort.

Although this specification discloses advantages in the context of certain illustrative, non-limiting embodiments, various changes, substitutions, permutations, and alterations may be made without departing from the scope of the appended claims. Further, any feature described in connection with any one embodiment may also be applicable to any other embodiment.

We claim:

1. A system for treating a tissue site, comprising:
   a tissue interface adapted to be positioned proximate to the tissue site;
   a dressing, comprising:
      a sealing member adapted to cover the tissue interface and the tissue site and to provide a sealed space between the sealing member and the tissue site, and
      a conduit interface positioned proximate to the sealing member and in fluid communication with the tissue interface;
   a reduced-pressure source adapted to provide a reduced pressure to the dressing;
   a therapy unit configured to receive a reduced-pressure feedback signal from the dressing; and
   a multi-lumen conduit comprising a wall carrying a primary lumen and at least one secondary lumen, the primary lumen in fluid communication between the dressing and the reduced-pressure source, the at least one secondary lumen in fluid communication between the dressing and the therapy unit, wherein the wall comprises a first wall material and a second wall material, the first wall material comprising a substantially non-absorbent material that is vapor impermeable and liquid impermeable, the second wall material comprising an absorbent material that is vapor permeable and liquid impermeable, the second wall material positioned in fluid contact with the at least one secondary lumen and forming at least a portion of an external surface of the multi-lumen conduit.

2. The system of claim 1, the tissue interface being adapted to distribute reduced pressure to the tissue site and comprising a porous hydrophobic material.

3. The system of claim 1, the sealing member being liquid impermeable and comprising polyurethane.

4. The system of claim 1, further comprising an adhesive disposed on a surface of the sealing member adapted to face the tissue site, the adhesive comprising an acrylic adhesive.

5. The system of claim 1, further comprising an absorbent layer disposed between the sealing member and the tissue interface, the absorbent layer comprising a hydrophilic material adapted to absorb fluid.

6. The system of claim 1, the absorbent material of the multi-lumen conduit being a hydrophilic polymer.

7. The system of claim 1, the conduit interface comprising an absorbent material that is vapor permeable and liquid impermeable, the absorbent material of the conduit interface being a hydrophilic polymer.

8. The system of claim 1, the reduced pressure provided through the primary lumen from the reduced-pressure source to the dressing, the reduced-pressure feedback signal provided through the at least one secondary lumen from the dressing to the therapy unit.

9. The system of claim 1, the primary lumen being in fluid communication between the conduit interface of the dressing and the reduced-pressure source, the at least one secondary lumen being in fluid communication between the conduit interface of the dressing and the therapy unit.

10. The system of claim 1, the primary lumen being substantially isolated from fluid communication with the at least one secondary lumen along a length of the multi-lumen conduit.

11. The system of claim 1, the at least one secondary lumen being disposed about a perimeter of the primary lumen.

12. The system of claim 1, an external surface of the multi-lumen conduit comprising a plurality of protrusions and depressions.

13. The system of claim 1, the absorbent material of the multi-lumen conduit having an unsaturated state being substantially free of vapor and a saturated state being fully saturated with vapor, a hardness of the absorbent material in the unsaturated state being substantially the same as a hardness of the absorbent material in the saturated state.

14. The system of claim 1, the second wall material defining the at least one secondary lumen.

15. The system of claim 1, the second wall material substantially surrounding the at least one secondary lumen.

16. The system of claim 1, the multi-lumen conduit comprising an external absorbent layer positioned at least around the second wall material, the external absorbent layer being comprised of a second absorbent material that is vapor permeable and liquid impermeable, the second absorbent material having a greater absorbent capacity than the second wall material.

17. The system of claim 1, the first wall material defining the primary lumen.

18. The system of claim 1, the multi-lumen conduit having an external surface comprised of the first material and the second material.

19. The system of claim 1, the at least one secondary lumen being a plurality of secondary lumens, the plurality of secondary lumens being disposed about a perimeter of the primary lumen.

20. The system of claim 19, the plurality of secondary lumens being disposed substantially equidistant about the perimeter of the primary lumen.

21. The system of claim 19, the plurality of secondary lumens being substantially isolated from fluid communication with one another along a length of the multi-lumen conduit.

22. The system of claim 1, the multi-lumen conduit comprising an external absorbent layer positioned around the wall of the multi-lumen conduit, the external absorbent layer being comprised of a second absorbent material that is vapor permeable and liquid impermeable, the second absorbent material having a greater absorbent capacity than the absorbent material of the wall.

23. The system of claim 1, the multi-lumen conduit having an unsaturated state being substantially free of vapor and a saturated state being fully saturated with vapor, a size of the multi-lumen conduit in the unsaturated state being substantially the same as a size of the multi-lumen conduit in the saturated state.

\* \* \* \* \*